United States Patent
Drager et al.

(10) Patent No.: US 11,071,789 B2
(45) Date of Patent: Jul. 27, 2021

(54) PHARMACEUTICAL PRODRUGS AND METHODS OF THEIR PREPARATION AND USE

(71) Applicant: CEPHALON, INC., North Wales, PA (US)

(72) Inventors: Anthony S. Drager, Thorndale, PA (US); Paritosh Wattamwar, Malvern, PA (US)

(73) Assignee: Cephalon, Inc., North Wales, PA (US)

( * ) Notice: Subject to any disclaimer, the term of this patent is extended or adjusted under 35 U.S.C. 154(b) by 0 days.

(21) Appl. No.: 16/316,451

(22) PCT Filed: Jul. 13, 2017

(86) PCT No.: PCT/US2017/041890
§ 371 (c)(1),
(2) Date: Jan. 9, 2019

(87) PCT Pub. No.: WO2018/013783
PCT Pub. Date: Jan. 18, 2018

(65) Prior Publication Data
US 2019/0240348 A1  Aug. 8, 2019

Related U.S. Application Data

(60) Provisional application No. 62/361,768, filed on Jul. 13, 2016.

(51) Int. Cl.
| | |
|---|---|
| *A61K 47/69* | (2017.01) |
| *A61K 47/54* | (2017.01) |
| *C07H 19/12* | (2006.01) |
| *C07H 15/24* | (2006.01) |
| *C07H 15/26* | (2006.01) |
| *A61K 9/51* | (2006.01) |
| *A61K 9/00* | (2006.01) |
| *A61K 31/415* | (2006.01) |
| *A61K 31/4184* | (2006.01) |
| *A61K 31/704* | (2006.01) |
| *A61K 38/00* | (2006.01) |

(52) U.S. Cl.
CPC ........ *A61K 47/6937* (2017.08); *A61K 9/0019* (2013.01); *A61K 9/5153* (2013.01); *A61K 31/415* (2013.01); *A61K 31/4184* (2013.01); *A61K 31/704* (2013.01); *A61K 47/54* (2017.08); *A61K 47/542* (2017.08); *A61K 47/543* (2017.08); *A61K 47/545* (2017.08); *C07H 15/24* (2013.01); *C07H 15/26* (2013.01); *C07H 19/12* (2013.01); *A61K 38/00* (2013.01)

(58) Field of Classification Search
CPC . A61K 47/6937; A61K 47/543; A61K 47/542
See application file for complete search history.

(56) References Cited

U.S. PATENT DOCUMENTS

| | | | |
|---|---|---|---|
| 9,452,988 B2 * | 9/2016 | Bakale | A61P 35/02 |
| 9,598,377 B2 | 3/2017 | Brown et al. | |
| 2015/0274675 A1 * | 10/2015 | Bakale | A61P 35/02 |
| | | | 514/394 |
| 2018/0360978 A1 * | 12/2018 | Blume-Jensen | A61K 9/146 |

FOREIGN PATENT DOCUMENTS

WO  2016/028700 A1  2/2016

OTHER PUBLICATIONS

Prabaharan M et al: "Amphiphilic multi-arm-block copolymer conjugated with doxorubicin via pH-sensitive hydrazone bond for tumor-targeted drug delivery", Biomaterials, vol. 30, No. 29, Oct. 1, 2009, pp. 5757-5766, XP026470002.
Manju et al: "Mechanisms and biomaterials in pH-responsive tumour targeted drug delivery: A review", Biomaterials, vol. 85, Jan. 29, 2016, pp. 152-167, XP029423187.
Dosio et al: "Novel Nanoassemblies Composed of Squalenoyl-Paclitaxel Derivatives: Synthesis, Characterization, and Biological Evaluation", Bioconjugate Chemistry, vol. 21, No. 7, Jul. 21, 2010, pp. 1349-1361, XP055406775.
Borrelli et al: "New class of squalene-based releasable nanoassemblies of paclitaxel, podophyllotoxin, camptothecin and epithilone A", European Journal of Medicinal Chemistry, vol. 85, Oct. 1, 2014, pp. 179-190, XP055406771.

* cited by examiner

*Primary Examiner* — Pancham Bakshi
(74) *Attorney, Agent, or Firm* — BakerHostetler

(57) ABSTRACT

The disclosure provides compounds of Formula (I), wherein X, Y, and Z are defined herein. The disclosure also provides particles comprising one or more compounds described herein, compositions comprising one or more compounds or particles described herein and a pharmaceutically acceptable carrier, and methods of treating a subject in need thereof comprising administering one or more compounds, particles, or compositions described herein to the subject.

X—Y—Z                                                        (I).

7 Claims, 16 Drawing Sheets

PHARMACEUTICAL PRODRUGS AND METHODS OF THEIR PREPARATION AND USE

CROSS-REFERENCE TO RELATED APPLICATIONS

This application is the National Stage Application of International Patent Application No. PCT/US2017/041890, filed Jul. 13, 2017, which claims priority of U.S. Provisional Patent Application No. 62/361,768, filed Jul. 13, 2016, which disclosures are herein incorporated by reference.

TECHNICAL FIELD

The disclosure relates to compounds, particles, and compositions that are useful in methods for treating subjects.

BACKGROUND

Prodrugs are often synthesized to either tune solubility of the drug, change pharmacokinetic behaviour of parent compound and/or to improve their encapsulation into particulate systems. In some applications, hydrophobic prodrugs are synthesized to improve their encapsulation in particulate systems with hydrophobic core. Prodrugs are designed to be retained in the core of these particles during systemic circulation, but also to be released and cleaved when the pH of the environment (e.g. tumor tissue) changes. However, there is a fine balance between hydrophobicity of the prodrug, loading efficiency and rate of release from the particle. For example, if the prodrug is highly hydrophobic, it may have higher loading efficiency but rate of release and biodegradation may be too slow. On the other hand, a relatively less hydrophobic drug may release and degrade at an acceptable rate, but will yield poor loading efficiencies.

Encapsulation of agents into polymer nanoparticles is one of the strategies utilized to improve drug efficacy and achieve targeted delivery while minimizing the undesired side-effects due to off-target drug toxicity. However, physical properties of the drugs often limit drug encapsulation efficiency, loading capacity and stability of polymer nanoparticle formulations.

What is needed is a prodrug approach to compounds and polymer nanoformulations in an effort to tune the pharmacokinetics and optimize overall efficacy of the nanoformulation.

SUMMARY

In some embodiments, the disclosure provides compounds of Formula (I), wherein X, Y, and Z are defined herein.

$$X—Y—Z \quad (I)$$

In other embodiments, the disclosure provides particles comprising one or more compounds of Formula (I) described herein. In some aspects, the particles are nanoparticles. In other embodiments, the particles are microparticles.

In further embodiments, the disclosure provides compositions comprising one or more particles described herein, and a pharmaceutically acceptable carrier.

In yet other embodiments, the disclosure provides methods of treating a subject in need thereof comprising administering to the subject, one or more compounds of Formula (I), particles, or compositions described herein.

DETAILED DESCRIPTION OF THE ILLUSTRATIVE EMBODIMENTS

Figure 1:
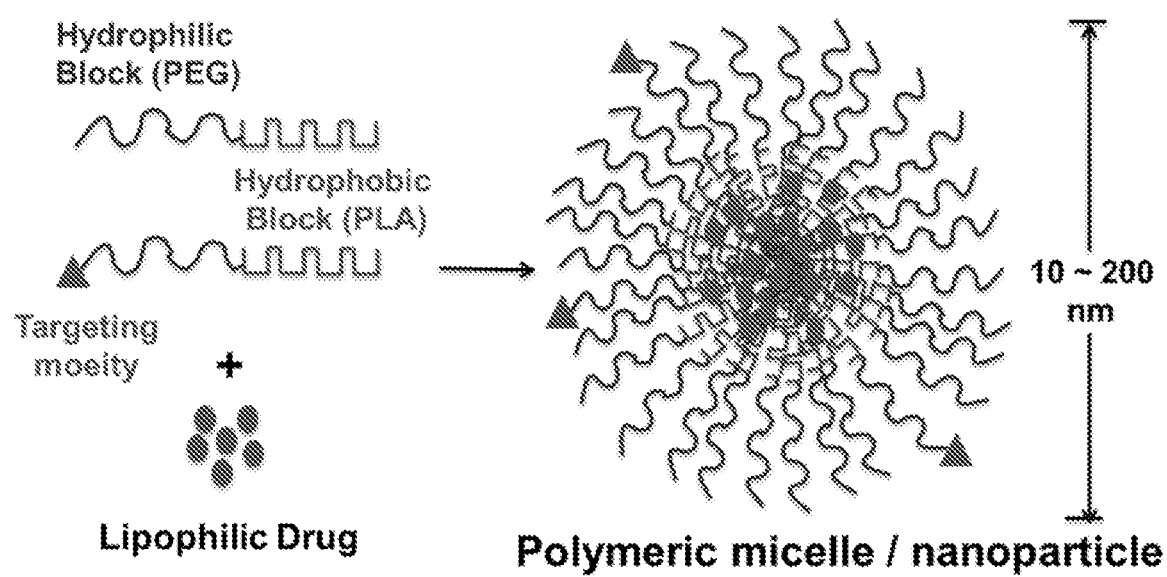
FIG. 1 is a schematic showing the preparation of diblock copolymers using a hydrophilic block (PEG), hydrophobic block (PLA), a targeting moiety, and lipophilic drug. The polymeric micelle/nanoparticle produced is about 10 to about 200 nm in size.

The present disclosure may be understood more readily by reference to the following detailed description taken in connection with the accompanying figures and examples, which form a part of this disclosure. It is to be understood that this disclosure is not limited to the specific compositions or methods described and/or shown herein, and that the terminology used herein is for the purpose of describing particular embodiments by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. All ranges are inclusive and combinable.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

The term "halogen," "halide," or "halo" includes fluorine, chlorine, bromine, and iodine.

"Alkyl" refers to substituted, optionally substituted and unsubstituted straight and branched carbon chains having 1 to 20 carbon atoms. Therefore, designated numbers of carbon atoms (e.g., $C_{1-20}$) refer independently to the number of carbon atoms in an alkyl moiety or to the alkyl portion of a larger alkyl-containing substituent. Preferably, alkyl includes a $C_{1-10}$alkyl, $C_{1-8}$alkyl, $C_{1-6}$alkyl, or $C_{1-4}$alkyl and, more preferably, $C_{1-6}$alkyl. For example, "alkyl" includes, but is not limited to, methyl (Me), ethyl (Et), propyl (Pr) such as isopropyl (i-Pr), butyl (Bu) such as isobutyl (i-Bu), tert-butyl (t-Bu), or sec-butyl (s-Bu), pentyl such as isopentyl or neopentyl, hexyl, heptyl, octyl, nonyl, decyl, or undecyl.

"Alkoxy" refers to an —O-alkyl group, wherein the term "alkyl" is as defined above.

The terms "alkenyl" and "alkynyl" refer to straight and branched carbon chains having 2 to 20 carbon atoms, wherein an alkenyl chain contains at least one double bond and an alkynyl chain contains at least one triple bond. Preferably, alkenyl includes a $C_{2-10}$alkenyl, $C_{2-8}$alkenyl, $C_{2-6}$alkenyl, or $C_{2-4}$alkenyl and, more preferably, $C_{2-6}$alkenyl. For example, "alkenyl" includes, but is not limited to, ethenyl, propenyl, butenyl, pentyl, hexenyl, heptenyl, octenyl, nonenyl, decenyl, or undecenyl. Preferably, alkynyl includes a $C_{2-10}$alkynyl, $C_{2-8}$alkynyl, $C_{2-6}$alkynyl, or $C_{2-4}$alkynyl and, more preferably, $C_{2-6}$alkynyl. For example, "alkynyl" includes, without limitation, ethynyl, propynyl, butynyl, pentynyl, hexynyl, heptynyl, octynyl, nonynyl, decynyl, or undecynyl, "Cycloalkyl" refers to saturated or partially saturated, monocyclic or polycyclic hydrocarbon rings of 3 to 14 carbon atoms. Preferably, alkyl includes a $C_{3-10}$cycloalkyl, $C_{3-8}$cycloalkyl, or $C_{3-6}$cycloalkyl and, more preferably, $C_{3-6}$cycloalkyl or $C_{3-8}$cycloalkyl. Examples of such rings include cyclopropyl, cyclobutyl, cyclopentyl, cyclohexyl, cycloheptyl, cyclooctyl, adamantly, cyclopentenyl, cyclohexenyl, cycloheptenyl, cyclooctenyl, methylcyclopropyl, ethylcyclohexenyl, butenylcyclopentyl, or norbornyl.

"Heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. "Heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are nonaromatic and at least one of the rings contains a heteroatom ring member. Examples of heterocycles include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

"Aryl" refers to an unsaturated, aromatic monocyclic or bicyclic ring of 6 to 10 carbon members. Examples of aryl rings include phenyl and naphthalenyl.

"Heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

"Optionally substituted" as used herein refers to a substituent where a hydrogen atom is replaced with a non-hydrogen atom or group. Suitable substituents include, without limitation, alkyl (e.g., methyl, ethyl, propyl, isopropyl, butyl, isobutyl, sec-butyl, t-butyl), cycloalkyl (e.g., cyclopropyl, cyclobutyl, cyclopentyl, cyclohexyl), halogen (i.e., F, Cl, Br, or I), CN, $NO_2$, COOH, C(O)R (wherein R is alkyl, cycloalkyl, heterocyclyl, heteroaryl, or aryl, C(O)OR (wherein R is alkyl, cycloalkyl, heterocyclyl, heteroaryl, or aryl), $NH_2$, NHR (wherein R is alkyl, cycloalkyl, heterocyclyl, heteroaryl, or aryl), $NR_2$ (wherein each R is, independently, alkyl, cycloalkyl, heterocyclyl, heteroaryl, or aryl), aryl, heteroaryl, heterocyclyl, $S(O)_2R$ (wherein R is, alkyl, cycloalkyl, heterocyclyl, heteroaryl, or aryl), or $S(O)_3R$ (wherein R is alkyl, cycloalkyl, heterocyclyl, heteroaryl, or aryl).

"Pharmaceutically acceptable" refers to physiologically tolerable materials, which do not typically produce an allergic or other adverse reaction when administered to a human.

"Pharmaceutically acceptable salts" are those derived from acids or bases (i.e., an acid addition salt or base addition salt, which salt is therapeutically active, non-toxic and otherwise acceptable for administration to a patient. Acid addition salts may be formed from compounds having an ionizable basic moiety by using a suitable acid reagent. Suitable acid reagents for forming an acid addition salt include inorganic acids such as hydrochloric, hydrobromic, sulfuric, sulfamic, phosphoric, nitric, and the like, as well as organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Base addition salts may be formed from compounds having an ionizable acidic moiety by using a suitable base reagent. Suitable base reagents for forming a base addition salt include inorganic bases such as alkali metal hydroxides such as sodium or potassium hydroxide, alkaline earth metal hydroxides such as calcium or magnesium hydroxide; and also include organic bases such as ammonia or amines such as triethyl amine or meglumine.

"Treatment" refers to the acute or prophylactic diminishment or alleviation of at least one symptom or characteristic associated or caused by a disorder being treated. In certain embodiments, treatment can include diminishment of several symptoms of a disorder or complete eradication of a disorder.

"Subject" includes mammals, preferably humans. The terms "human," "patient," and "subject" are used interchangeably herein.

The present disclosure provides compounds of Formula (I) which act as prodrugs, as described herein. The compounds of Formula (I), when encapsulated in particles (e.g., nanoparticles), were found to have a long circulation time and advantageously cross the membranes of cells, effecting invasion and/or death of undesirable cells such as cancer cells. Advantageously, these compounds of Formula (I) and particles containing them do not infiltrate into healthy tissues, which should reduce the likelihood of potential side effects. The log P of these compounds of Formula (I) is about 7 or greater such as about 8 or greater, about 9 or greater, about 10 or greater, about 11 or greater, about 12 or greater, about 13 or greater, about 14 or greater, or about 15 or greater.

These compounds include compounds of Formula (I):

X—Y—Z  (I)

In Formula (I), X is a biologically active moiety derived from a water-soluble, biologically active compound. The term "water-soluble" as used herein refers a chemical compound having a solubility in water, that is, having a solubility in water of greater than 0 mg/mL. Thus, in some embodiments, the term "water-soluble" includes chemical compounds that are sparingly soluble. In other embodiments, the biologically active compound has a water-solubility of about 0.001 to greater than or equal to about 1000 mg/mL. In further embodiments, the biologically active compound has a water-solubility of about 1 mg/mL to greater than or equal to about 1000 mg/mL. In other embodiments, the biologically active compound has a water solubility of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, or about 1000 mg/mL. In other embodiments, the biologically active compound has a water solubility of 1000 mg/mL or greater.

The water-soluble, biologically active moiety is derived from a water-soluble, biologically active compound. The term "derived" refers to biologically active compound that has been modified so as to covalently bond to Y—Z. In some embodiments, the water-soluble, biologically active compound contains a functional group that can be modified for covalent bonding to Y or Y—Z. Examples of such moieties include, without limitation, alkenyl, alkynyl, COOH, OH, amine such as $N_3$, thiol, amines, among others. Preferred moieties include —COOH, —OH, amines such as primary and secondary amines, and thiol.

The term "biologically active" refers to the ability of a compound described herein to effect a biological change in a subject, modulate a biological receptor or mechanism, or have a physiological effect in a subject.

In some embodiments, the water-soluble, biologically active compound has a relatively short half-life. In other embodiments, the water-soluble, biologically active compound has a half-life that negatively affects the therapeutic effect of the compound in vivo. In further embodiments, the partition coefficient (log P) of the water-soluble, biologically active compound is about 7 or less such as about 6.5 or less, about 6 or less, about 5.5 or less, about 5 or less, about 4.5 or less, about 4 or less, about 3.5 or less, about 3 or less, about 2.5 or less, or about 2 or less.

The water-soluble, biologically active compound may be selected by one skilled in the art depending on the condition being treated. Selection of the water-soluble, biologically active compound may also depend on other factors including, without limitation, components of the composition, mode of delivery, severity of the condition being treated, the patient's age and weight, and any other active ingredients used in the composition.

In some embodiments, the water-soluble, biologically active compound is an anti-inflammatory agent, anti-psychotic agent, anti-viral agent, chemotherapeutic agent, or dopamine modulating agent, or is indicated for the treatment of migraine or pain. In other embodiments, the water-soluble, biologically active compound is an anti-inflammatory agent. In further embodiments, the water-soluble, biologically active compound is an anti-psychotic agent. In yet other embodiments, the water-soluble, biologically active compound is an anti-viral agent. In still further embodiments, the water-soluble, biologically active compound is a chemotherapeutic agent. In yet other embodiments, the water-soluble, biologically active compound is a dopamine modulating agent. In further embodiments, the water-soluble, biologically active compound is indicated for the treatment of migraine. In other embodiments, the water-soluble, biologically active compound is indicated for the treatment of pain. As those skilled in the art will appreciate, some water-soluble, biologically active compound useful herein may have one mechanism of action or two or more mechanisms of action. For example, a single water-soluble, biologically active compound may be categorized as both an anti-inflammatory agent and indicated for the treatment of migraine or pain.

As discussed above, the water-soluble biologically active compound may be selected by one skilled in the art. In some embodiments, the water-soluble, biologically active compound is actinomycin, azacitidine, belinostat, bendamustine, bleomycin, bortezomib, cabazitaxel, cadarbazine, cladribine, clofarabine, cytarabine, cyproterone, daunorubicin, decitabine, docetaxel, doxorubicin, epirubicin, eribulin, etoposide, floxuridine, fludarabine, gemcitabine, idarubicin, irinotecan, ixabepilone, levodopa, melphalan, methotrexate, mitomycin, mitoxantrone, nelarabine, olanzapine, paclitaxel, pemetrexed, pentostatin, pixantrone, pralatreate, raltitrexed, streptozocin, temozolomide, temsirolimus, teniposide, topotecan, trabectedin, treosulfan, vincristine, vindesine, vinflunine, or a salt thereof. In other embodiments, the water-soluble, biologically active compound is bendamustine, decitabine, doxorubicin, celecoxib, or a salt thereof. In further embodiments, the water-soluble, biologically active compound is bendamustine or a salt thereof. In other embodiments, the water-soluble, biologically active compound is decitabine or a salt thereof. In still further embodiments, the water-soluble, biologically active compound is doxorubicin or a salt thereof. In yet other embodiments, the water-soluble, biologically active compound is celecoxib or a salt thereof.

The water-soluble, biologically active compound may also comprise a nucleoside. Thus, in some embodiments, the water-soluble, biologically active compound is abacavir, didanosine, emtricitabine, lamivudine, stavudine, telbivudine, entecavir, or a salt thereof. In other embodiments, the biologically active compound is levodopa. Pharmaceutical compositions of the disclosure that include levodopa as the biologically active compound can effect kinetic control of, for example, an orally dosed, thereby preventing $C_{max}$ driven, levodopa side effects.

Derivatives of the biologically active compounds are also contemplated for use as described herein. The term "derivative" as used herein refers to a compound having the core backbone of the biologically active compound, but modified to so that the structure is changed, but the activity of the biologically active compound is not changed or otherwise affected. The modification typically includes replacing one or more atoms at any position of the molecule with another atom or group. For example, the term "bendamustine derivative" refers to a compound having the following generic structure, but modified by replacing one or more atom with another atom or group.

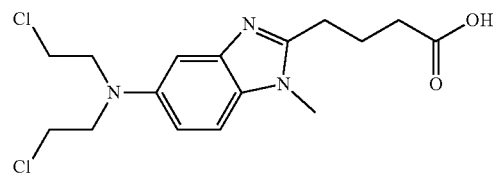 [SMILES: Cn1c(CCCC(=O)O)nc2cc(N(CCCl)CCCl)ccc21]

The water-soluble, biologically active compounds which are suitable also include such water-soluble, biologically active compounds wherein the molecular structures include isotopes of carbon, hydrogen and nitrogen atoms occurring on those structures. Isotopes include those atoms having the same atomic number but different mass numbers. For example, isotopes of hydrogen include deuterium. Isotopes of carbon include C-13. Isotopes of nitrogen include N-15. Accordingly, one or more atom within the chemical structure of any water-soluble, biologically active compound discussed herein may be an isotope. In some embodiments, any hydrogen atom or group of hydrogen atoms may be replaced by an isotope of hydrogen, i.e., deuterium. In other embodiments, any carbon atom or group of carbon atoms may be replaced by an isotope of carbon, i.e., $^{13}C$. In further embodiments, any nitrogen atom or group of nitrogen atoms may be replaced by an isotope of nitrogen, i.e., $^{15}N$.

Y in Formula (I) comprises a pH-sensitive linker. The term "pH-sensitive" as used herein refers to the ability of the linker to be affected by the pH surrounding the linker. In some embodiments, the pH-sensitivity of the linker results in Y being cleaved from the water-soluble, biologically active moiety upon exposure to a target pH. The term "cleaved" as used herein refers to breaking of the covalent bond between the X and Y groups. In doing so, the compound of Formula (I) releases the water soluble biologically active compound. In preferred embodiments, the compound of Formula (I) releases the water soluble biologically active compound within a cell after crossing the cell membrane.

Desirably, Y is cleaved at a target pH. In some embodiments, the "target pH" refers to the pH of a cell or tissue in a patient which is receptive to action by the water-soluble, biologically active compound. Preferably, the target pH is the pH at or in a tumor/cancer cell, an inflammation-associated cell, or the like. Thus, in these embodiments, the target pH is less than about 7. In other embodiments, the target pH is about 5 to about 7, about 5.2 to about 6.8, about 5.4 to about 6.6, about 5.6 to about 6.4, or about 5.8 to about 6.2. In other embodiments, the "target pH" refers to a gastric pH such as a pH of below about 7. In further embodiments, the gastric pH is about 1 to about 6.9, about 2 to about 6.5, about 3 to about 6, about 1, about 2, about 3, about 4, about 6, or about 6.5. Desirably, cleavage is performed with hydrolysis.

Y may be one or more pH sensitive linkers. In some embodiments, Y comprises 1 to about 5 pH sensitive linkers. In further embodiments, Y is a single pH sensitive linker. In other embodiments, Y comprises a first pH sensitive linker and a second pH sensitive linker. In yet further embodiments, Y comprises a first pH sensitive linker, a second pH sensitive linker, and a third pH sensitive linker. In still other embodiments, Y comprises a first pH sensitive linker, a second pH sensitive linker, a third pH sensitive linker, and a fourth pH sensitive linker. In further embodiments, Y comprises a first pH sensitive linker, a second pH sensitive linker, a third pH sensitive linker, a fourth pH sensitive linker, and a fifth pH sensitive linker.

In some embodiments, Y comprises an optionally substituted tetrahydropyranyl ether, an optionally substituted tetrahydropyranyl ester, an optionally substituted azide, an optionally substituted histidine, an optionally substituted hydrazone, or an optionally substituted β-amino ester. In some embodiments, Y is an optionally substituted tetrahydropyranyl ether such as -(tetrahydropyran ether)- or -(tetrahydropyran ether)-(azide)-. In one example, Y is

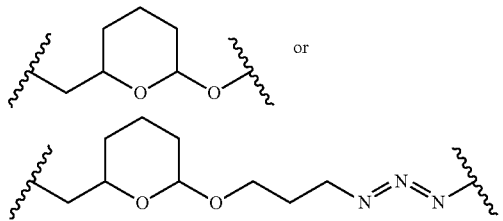

In other embodiments, Y is an optionally substituted tetrahydropyranyl ester such as -(tetrahydropyran ester)-. In another example, Y is

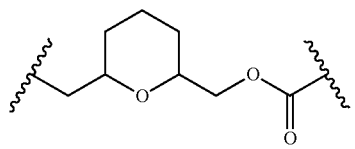 [SMILES: *CC1CCCC(COC(*)=O)O1]

In further embodiments, Y is an optionally substituted azide such as -(tetrahydropyran ether)-(azide)-, -(hydrazone)-(azide)-, or -(β-amino ester)-(azide)-. In a further example, Y is:

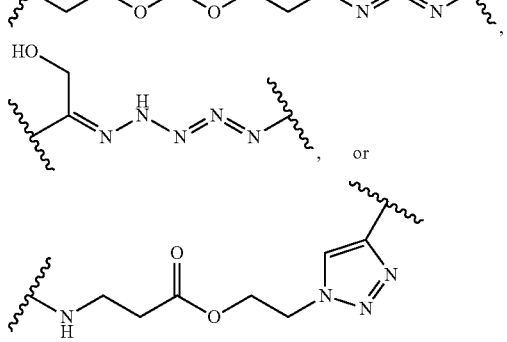

In still other embodiments, Y is an optionally substituted histidine. In another example, Y is

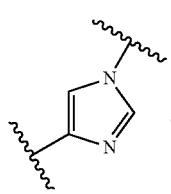

In yet further embodiments, Y is an optionally substituted hydrazone such as -(hydrazone)- or -(hydrazone)-(azide)-. In yet another example, Y is

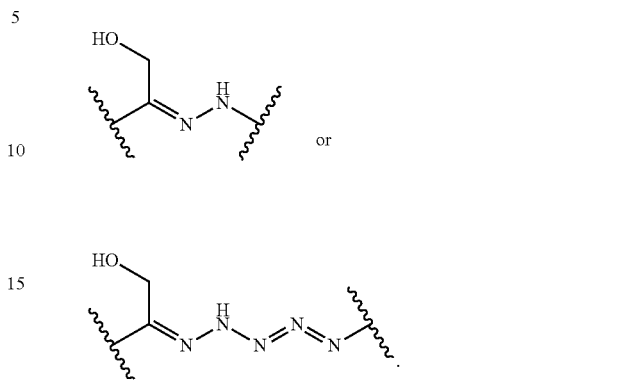

In other embodiments, Y is an optionally substituted β-amino ester such as -(β-amino ester)- or -(β-amino ester)-(azide)-. In a further example, Y is

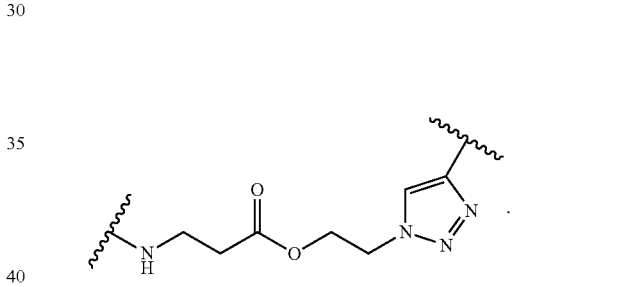

As noted above, Y may comprise a first pH sensitive linker and a second pH sensitive linker. In some embodiments, one of the pH-sensitive linkers enhances the solubility of the compound of Formula (I) at the target pH as described above. In other embodiments, one pH-sensitive linker is a histidine or hydrazone moiety.

In some embodiments, the second pH sensitive linker comprises a histidine. Thus, in further embodiments, Y may comprise -(tetrahydropyran ether)-(azide)-(His), -(hydrazone)-(azide)-(His)-, or -(β-amino ester)-(azide)-(His)-.

In some embodiments, Y is -(tetrahydropyran ether)-(azide)-(His)-. In one example, Y is

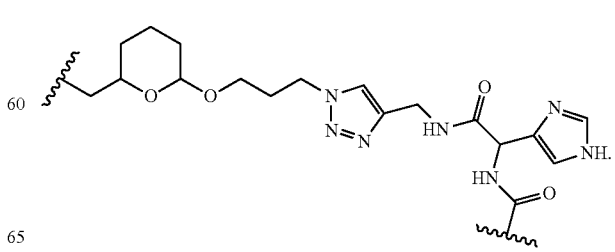

In further embodiments, Y is -(hydrazone)-(azide)-(His)-. In another example, Y is

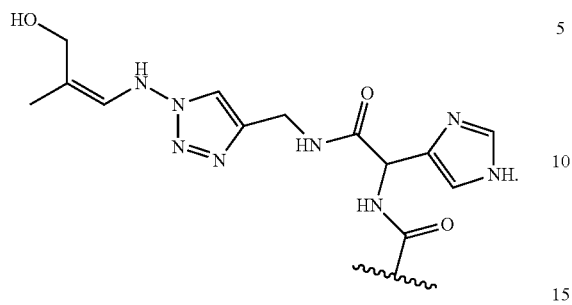

In other embodiments, Y is -(β-amino ester)-(azide)-(His)-. In a further example, Y is

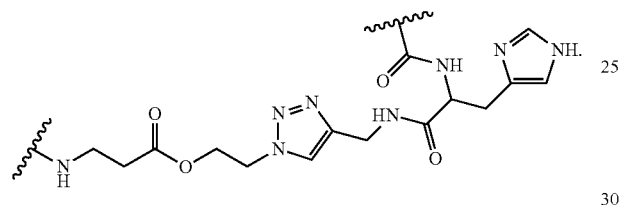

Z in Formula (A) is a hydrophobic moiety. The term "hydrophobic" as used herein refers to a nonpolar moiety that aggregates in aqueous solution and excludes water molecules. Without desiring to be held to any particular theory, is it believed that Z enhances the circulation time of the compound of Formula (I). In some embodiments, Z is an optionally substituted $C_{2-30}$alkyl, $C_{2-30}$alkenyl, or $C_{2-30}$alkynyl. In other embodiments, Z is an optionally substituted $C_{2-18}$alkyl such as $C_{12}$alkyl, $C_{14}$alkyl, $C_{16}$alkyl, or $C_{18}$alkyl. In further embodiments, Z is an optionally substituted $C_{2-18}$alkenyl such as $C_{12}$alkenyl, $C_{14}$alkenyl, $C_{16}$alkenyl, or $C_{18}$alkenyl. In other embodiments, Z is an optionally substituted $C_{2-18}$alkynyl such as $C_{12}$alkynyl, $C_{14}$alkynyl, $C_{16}$alkynyl, or $C_{18}$alkynyl.

In some embodiments, in the compound of Formula (I), X is a bendamustine moiety, Y is a tetrahydropyran ether, and Z is $C_{2-20}$alkyl. For example, the compound of Formula (I) is:

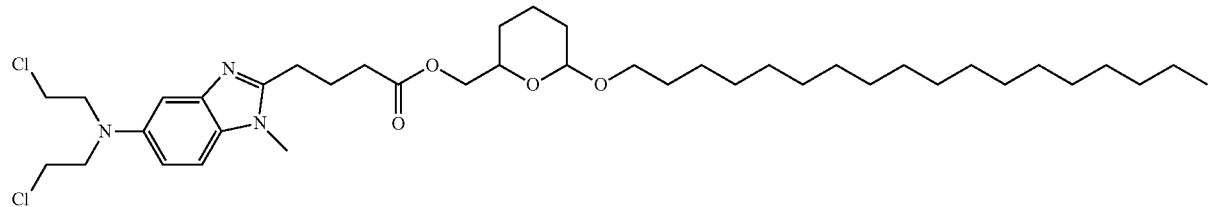 [SMILES: CCCCCCCCCCCCCCCCCCOC1CCCC(COC(=O)CCCc2nc3cc(N(CCCl)CCCl)ccc3n2C)O1]

In other embodiments, in the compound of Formula (I), X is a bendamustine moiety, Y comprises three pH-sensitive linkers, and Z is $C_{2-20}$alkyl. In certain aspects, Y comprises a tetrahydropyran ether, an azide, and a histidine. For example, the compound of Formula (I) is:

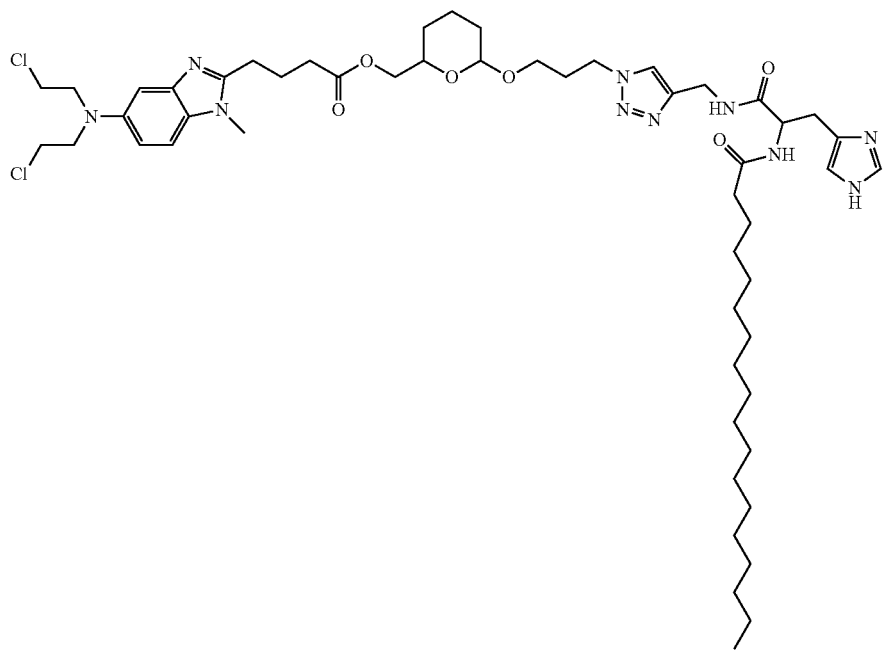 [SMILES: CCCCCCCCCCCCCCCCCC(=O)NC(Cc1c[nH]cn1)C(=O)NCc1cn(CCCOC2CCCC(COC(=O)CCCc3nc4cc(N(CCCl)CCCl)ccc4n3C)O2)nn1]
In further embodiments, in the compound of Formula (I), X is a doxorubicin moiety, Y comprises a hydrazone, and Z is $C_{2-20}$alkyl. For example, the compound of Formula (I) is:
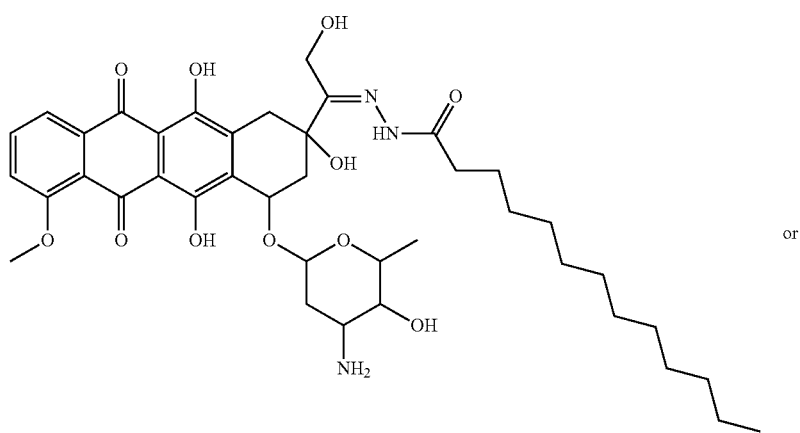
or -continued

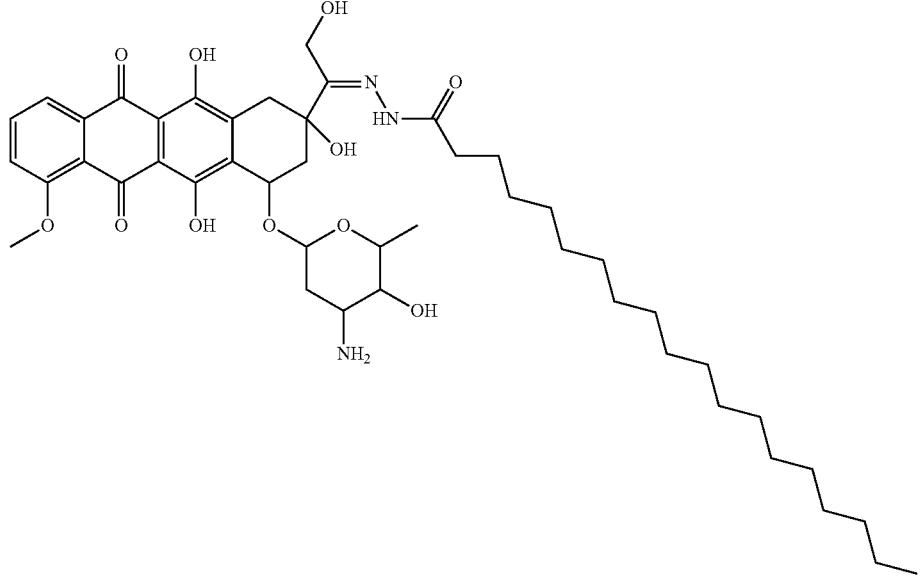

In further embodiments, in the compound of Formula (I), X is a doxorubicin moiety, Y comprises three pH-sensitive linkers, and Z is $C_{2-20}$alkyl. In some aspects, X is a doxorubicin moiety, Y comprises a hydrazone, azide, and histidine, and Z is $C_{2-20}$alkyl. For example, the compound of Formula (I) is:

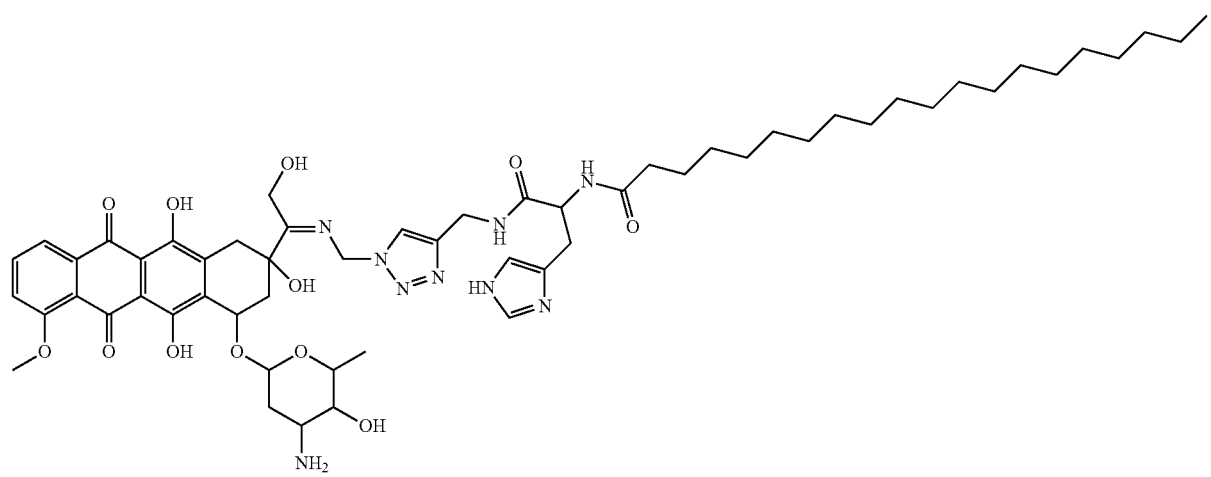 [SMILES: CCCCCCCCCCCCCCCCCCCC(=O)NC(Cc1c[nH]cn1)C(=O)NCc1cn(C/N=C(/CO)C2(O)Cc3c(O)c4c(c(O)c3C(OC3CC(N)C(O)C(C)O3)C2)C(=O)c2c(OC)cccc2C4=O)nn1]

In further embodiments, in the compound of Formula (I), X is a celecoxib moiety, Y is a β-amino ester, and Z is $C_{2-20}$alkyl. For example, the compound of Formula (I) is:

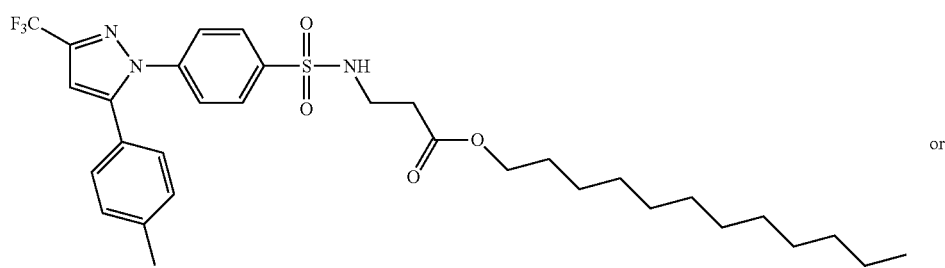

or

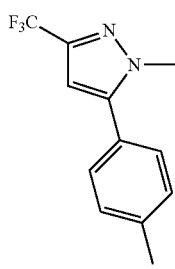

15

In yet other embodiments, in the compound of Formula (I), X is a celecoxib moiety, Y comprises three pH-sensitive linkers, and Z is C$_{2-20}$alkyl. In some aspects, Y comprises a β-amino ester, azide, and histidine. For example, the compound of Formula (I) is:

The compounds of Formula (I) of the disclosure may be prepared in light of the specification using steps generally known to those of ordinary skill in the art. Those compounds of Formula (I) may be analyzed by known methods, including but not limited to LCMS (liquid chromatography mass spectrometry) and NMR (nuclear magnetic resonance). Below are a set of generic schemes that illustrate generally how to prepare the compounds of Formula (I) of the present disclosure.

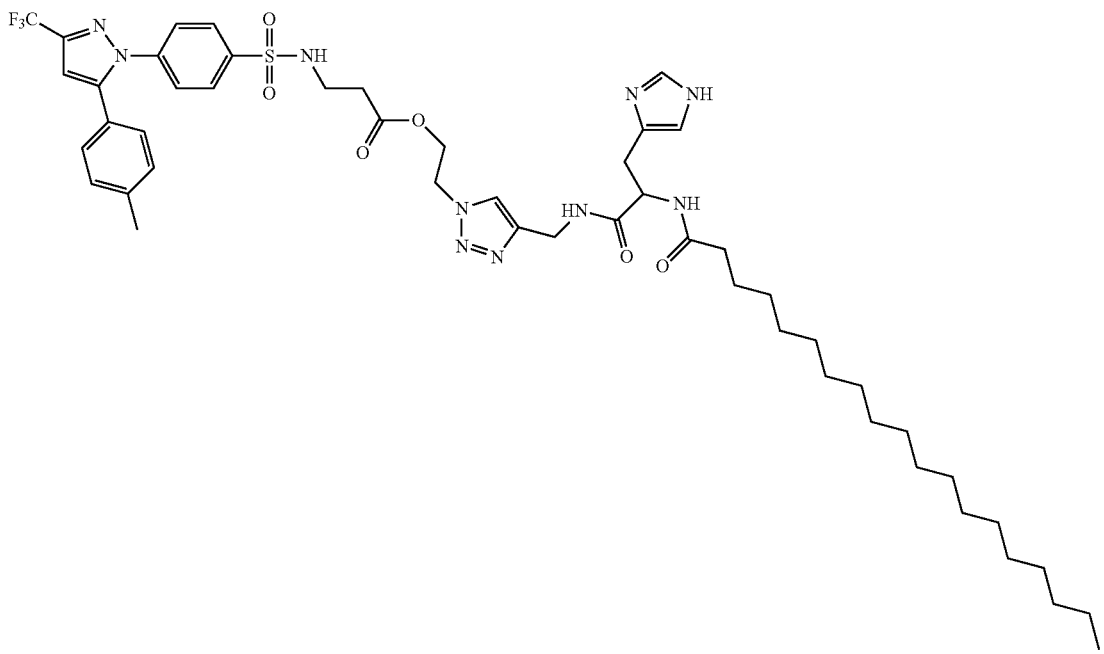 [SMILES: CCCCCCCCCCCCCCCCCCC(=O)NC(Cc1c[nH]cn1)C(=O)NCc1cn(CCOC(=O)CCNS(=O)(=O)c2ccc(-n3nc(C(F)(F)F)cc3-c3ccc(C)cc3)cc2)nn1]

In still further embodiments, in the compound of Formula (I), X is a decitabine moiety, Y is a tetrahydropyran ester, and Z is C$_{2-20}$alkyl. For example, the compound of Formula (I) is:

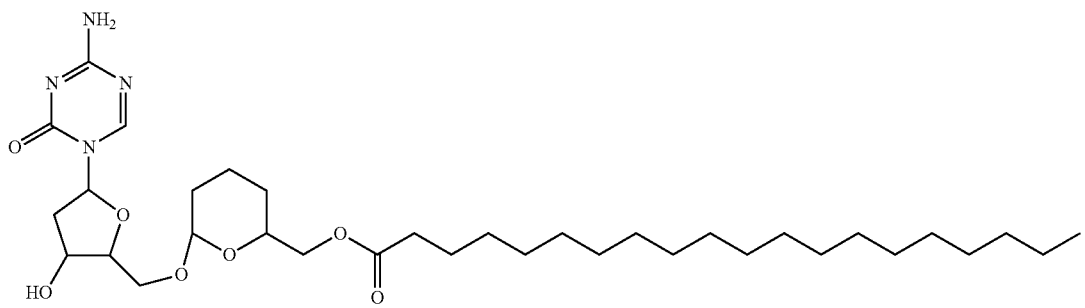 [SMILES: CCCCCCCCCCCCCCCCCCCC(=O)OCC1CCCC(OCC2OC(n3cnc(N)nc3=O)CC2O)O1]

Regardless of the physical form, the disclosure also provides particles which contain a compound of Formula (I) herein. Within the scope of the invention, "particles" are nanoparticles, microparticles, or macroparticles, or combinations thereof. In some embodiments, the particles are nano-particles. "Nanoparticles" are understood in the art to have an average diameter of between about 10 nm and 200 nm. Preferably, the nanoparticles have an average particle size of about 20 to about 190, about 30 to about 180, about 40 to about 170, about 50 to about 180, about 60 to about 170, about 70 to about 160, about 80 to about 150, about 90 to about 140, about 100 to about 130, or about 50 to about 150 nm. In other embodiments, the particles are microparticles. The nanoparticles may also include those described in U.S. Pat. No. 9,598,377, which is incorporated by reference herein. In some embodiments, the nanoparticles may be prepared using methods known in the art to form the desired particle size.

"Microparticles" formed according to the invention are understood in the art to have an average diameter of about 1 to about 200 µm. Preferably, the microparticles have an average particle size of about 5 to about 190, about 10 to about 180, about 20 to about 170, about 30 to about 160, about 40 to about 150, about 50 to about 140, about 60 to about 130, about 70 to about 12, about 80 to about 110, or about 90 to about 100 µm.

"Macroparticles" formed according to the invention are understood in the art to have an average diameter of greater than about 200 µm. Preferably, the macroparticles have an average particle size of about 250 to about 1000 µm. In some aspects, the macroparticles have an average particle size of greater than about 1000 µm.

Particle size determination for any of the materials of the invention can be achieved using any methods known in the art. Suitable methods for particle size determination include dynamic light scattering (DLS) or transmission electron microscopy (TEM) methods. As used herein, the term "particles" refers to granules, spheroids, beads, or pellets that comprise one or more compound of Formula (I). The disclosed particles can be prepared using any of the components and/or methods described herein.

The nano-particles useful as described herein further comprise a low molecular weight polymer. In some embodiments, the polymer is a diblock or triblock copolymer. In other embodiments, the polymer is a diblock copolymer. In further embodiments, the polymer is a triblock polymer.

The term "molecular weight" as used herein to describe a polymer refers to the $M_w$.

$$M_w = \frac{\sum N_i M_i^2}{\sum N_i M_i}$$

where $M_i$ is the molecular weight of a chain and $N_i$ is the number of chains of that molecular weight.

Preferably, at least one block of the polymer comprises a water soluble polymer. Water-soluble polymers may be selected by those skilled in the art and include, without limitation, a polyethylene glycol. In some embodiments, the first block polymer such as polyethylene glycol has a molecular weight of, for example, about 400 to about 5000 Da. In other embodiments, the first block polymer such as polyethylene glycol has a molecular weight of less than about 400 Da. In other embodiments, the first block polymer such as polyethylene glycol has a molecular weight of greater than 5000 Da. For example, the polyethylene glycol may have a molecular weight of about 500 to about 4800, about 600 to about 4700, about 700 to about 4600, about 800 to about 4500, about 900 to about 4400, about 1000 to about 4300, about 1100 to about 4200, about 1200 to about 4100, about 1300 to about 4000, about 1400 to about 3900, about 1500 to about 3800, about 1600 to about 3700, about 1700 to about 3600, about 1800 to about 3500, about 1900 to about 3400, about 2000 to about 3300, about 2100 to about 3200, about 2200 to about 3100, about 2300 to about 3000, about 400 to about 2000, about 400 to about 2500, about 400 to about 3000, about 400 to about 4000, about 1500 to about 2000, about 1500 to about 2500, about 1500 to about 3000, about 1500 to about 3500, about 1500 to about 4000, or about 1500 to about 4500 Da.

Preferably, a second block of the polymer comprises a biodegradable, hydrophobic polymer. The term "biodegradable" as used herein to describe the polymer refers to the ability of polymer to degrade under biologically relevant conditions in the presence of esterases and/or water for hydrolysis. In some embodiments, the second block polymer has a molecular weight of about 1000 to about 50000 Da. For example, the second block polymer has a molecular weight of about 2000 to about 45000, about 3000 to about 40000, about 4000 to about 35000, about 5000 to about 30000, about 6000 to about 25000, about 1000 to about 30000, about 1000 to about 35000, about 1000 to about 40000, about 1000 to about 45000, about 10000 to about 35000, about 10000 to about 40000, about 10000 to about 45000, about 20000 to about 40000, or about 20000 to about 45000, or about 20000 to about 50000 Da. In other embodiments, the second block is a poly(ethylene glycol)-b-poly(lactic acid) polymer, poly(lactic-co-glycolic acid), poly(caprolactone), or combinations thereof. In further embodiments, the second black is a poly(ethylene glycol)-b-poly(lactic acid) polymer. In yet other embodiments, the second block is a poly(lactic-co-glycolic acid) polymer. In still further embodiments, the second block is a poly(caprolactone).

The second block may optionally comprise a pH-sensitive polymer. In some embodiments, the polymer is a diblock polymer wherein one block is a pH-sensitive polymer. In other embodiments, the polymer is a diblock polymer wherein two blocks of the polymer are linked with a pH-sensitive polymer. The term "pH-sensitive polymer" as used herein refers to the ability of the polymer to be affected by the pH surrounding the polymer. In some embodiments, the pH-sensitivity of the polymer results in one or bonds in the compound of Formula (I) being broken upon exposure to a target pH. In some embodiments, the bonds within Y are cleaved upon exposure to a target pH. In doing so, the bonds within the diblock or triblock polymer are cleaved and the compound of Formula (I) "releases" the water soluble biological compound after crossing the cell membrane of a cell. In some embodiments, the pH-sensitive polymer is cleaved at a target pH as previously described. Thus, in some embodiments, the target pH is less than about 7. In other embodiments, the target pH is about 5 to about 7, about 5.2 to about 6.8, about 5.4 to about 6.6, about 5.6 to about 6.4, or about 5.8 to about 6.2. The pH-sensitive polymer may be selected from those known in the art. Preferably, the pH-sensitive polymer is poly(histidine).

The compounds of Formula (I) and particles containing them may be used, alone or in combination with one or more additional optional active ingredients, to formulate pharmaceutical compositions. In some embodiments, pharmaceutical compositions comprise a compound of Formula (I) and a pharmaceutically acceptable excipient. In other embodiments, the pharmaceutical compositions comprise particles which comprise a compound of Formula (I) and a pharmaceutically acceptable excipient.

The amount of the compound of Formula (I) or particles which comprise a compound of Formula (I) included in the compositions described herein may be determined by one of skilled in the art, i.e., can be any useful amount. In some embodiments, the compound of Formula (I) may be determined using The Physician's Desk Reference, 70$^{th}$ Edition, 2016. In other embodiments, the amount of the compound of Formula (I) is sufficient to induce a beneficial therapeutic response in the patient over time. The beneficial dose can vary from patient to patient depending upon the patient's condition, body weight, surface area, and side effect susceptibility, among others. Administration can be accomplished via single or divided doses. "Therapeutically effective amount" or "effective amount" refers to an amount of a water-soluble, biologically active compound described herein which is sufficient to inhibit, halt, or cause an improvement in a disorder or condition being treated in a particular subject or subject population. In certain embodiments, in a human or other mammal, a therapeutically effective amount can be determined experimentally in a laboratory or clinical setting, or may be the amount required by government guidelines for the particular disease and subject being treated. It should be appreciated that determination of proper dosage forms, dosage amounts, and routes of administration is within the level of ordinary skill in the pharmaceutical and medical arts.

Delivery forms of the pharmaceutical compositions containing one or more dosage units of the compound of Formula (I) and/or particles containing same may be prepared using suitable pharmaceutical excipients and compounding techniques known or that become available to those skilled in the art. The compositions may be administered by a suitable route of delivery, e.g., oral, parenteral including intravenous, intramuscular, intraperitoneal, or subcutaneous routes, rectal, topical, or ocular routes, or by inhalation. The preparation may be in the form of tablets, capsules, sachets, syrups, dragees, powders, granules, lozenges, powders for reconstitution, liquid preparations such as suspensions, emulsions, dispersions, gels such as in-situ forming gels, depot, or suppositories. In some embodiments, the composition is the form of a suspension, emulsion, dispersion, or depot. In other embodiments, the compositions are formulated for intravenous infusion, topical administration, or oral administration. In further embodiments, the compositions are formulated for oral administration, optionally wherein the compounds of formula (I) are encapsulated by macroparticles. In yet other embodiments, the compositions are formulated for depot administration, optionally wherein the compounds of formula (I) are encapsulated by macroparticles. Regardless of the mode of delivery, the compositions may contain one or more pharmaceutically acceptable excipient. "Pharmaceutically acceptable excipients" include, but not limited to, diluents, disintegrants, binders and lubricants. Preferably, the excipients meet the standards of the National Formulary or United States Pharmacopoeia. Examples of suitable excipients include, without limitation, diluents including waters or oils, fillers, disintegrants, binders, lubricants, sweetening agents, flavoring agents, coloring agents and preservatives, suspending agents, non-aqueous vehicles, or wetting agents.

Also provided herein are kits or packages of pharmaceutical formulations containing one or more compounds of Formula (I) or salts thereof, particles containing the compounds of Formula (I), or pharmaceutical compositions described herein. The kits may be organized to indicate a single formulation or combination of formulations to be taken at each desired time. The composition may also be sub-divided to contain appropriate quantities of one or more compound of Formula (I) or salts thereof, particles containing the compounds of Formula (I), or pharmaceutical compositions described herein. For example, the unit dosage can be packaged compositions, e.g., packeted powders, vials, ampoules, prefilled syringes or sachets containing liquids.

Suitably, the kit contains packaging or a container with the one or more compound of Formula (I) or salts thereof, particles containing the compounds of Formula (I), or pharmaceutical compositions described herein formulated for the desired delivery route. Suitably, the kit contains instructions on dosing and an insert regarding the one or more compound of Formula (I) or salts thereof, particles containing the compounds of Formula (I), or pharmaceutical compositions described herein. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The one or more compound of Formula (I) or salts thereof, particles containing the compounds of Formula (I), or pharmaceutical compositions described herein can be a single dose or for continuous or periodic discontinuous administration. For continuous administration, a package or kit can include the compound of Formula (I) in each dosage unit (e.g., solution, lotion, tablet, pill, or other unit described above or utilized in drug delivery). When the one or more compound of Formula (I) or salts thereof, particles containing the compounds of Formula (I), or pharmaceutical compositions described herein is to be delivered with periodic discontinuation, a package or kit can include placebos during periods when the one or more compound of Formula (I) or salts thereof, particles containing the compounds of Formula (I), or pharmaceutical compositions described herein is not delivered. When varying concentrations of a composition, of the components of the composition, or of relative ratios of the one or more compound of Formula (I) or salts thereof or particles containing the compounds of Formula (I), or other agents within a composition over time is desired, a package or kit may contain a sequence of dosage units, so varying.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The one or more compound of Formula (I) or salts thereof, particles containing the compounds of Formula (I), or pharmaceutical compositions of these kits also may be provided in dried or lyophilized forms. When reagents or components are provided as a dried form, reconstitution generally is by the addition of a suitable solvent. It is envisioned that the solvent also may be provided in another packaging means.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In treatment methods according to the disclosure, an effective amount of a compound of Formula (I), particles containing a compound of Formula (I), and/or composition containing the compound of Formula (I) and/or particles containing a compound of Formula (I) is administered to a subject. In some embodiments, the subject suffers from or is diagnosed as having such a disease, disorder, or condition. The disease, disorder, or condition is dependent upon the mechanism of action of the water-soluble, biologically active compound.

Thus, the compounds of Formula (I) and particles containing same are useful in treating a variety of diseases, disorders, and/or conditions. In some embodiments, the disease, disorder, or condition is cancer, inflammation, virus infection, psychosis, a dopamine-related disease, or pain. In other embodiments, the subject is infected with a virus. In some aspects, the virus is hepatitis such as hepatitis A, B, or C. In other aspects, the virus is human immunodeficiency virus (HIV).

In further embodiments, the subject is afflicted with pain. The term "pain" as used herein includes all types of pain. The pain may be acute, chronic, nociceptive, dysfunctional, idiopathic, neuropathic, somatic, visceral, inflammatory, and/or procedural. In some aspects, the pain may be from a migraine, back pain, neck pain, gynecological pain, pre-labor or labor pain, orthopedic pain, post-stroke pain, post-surgical or procedural pain, post herpetic neuralgia, sickle cell crises, interstitial cystitis, urological pain, dental pain, headache, pain from a wound or from a medical procedure such as surgery, suturing, setting a fracture, biopsy, and the like. Pain may also occur in patients with cancer. In other aspects, the pain is migraine pain.

In still other embodiments, the disease is cancer. In some aspects, the cancer is a hematological cancer or tumor. In other embodiment, the cancer is a solid tumor. In further aspects, the cancer is acute lymphocytic leukemia (relapsed, refractory acute lymphoblastic leukemia, or childhood), acute myeloid leukemia, adrenocortical carcinoma, anal cancer, appendix cancer, B-cell chronic lymphocytic leukemia, bile-duct cancer, bone cancer, bladder cancer, brain cancer, bronchial tumor, breast cancer including advanced and metastatic, Burkitt lymphoma, cancers of the Islets of Langerhans, central nerve system cancer, cervical cancer, chondrosarcoma, chronic myelomonocytic leukemia, chronic lymphocytic leukemia, chronic myelogenous leukemia, colorectal cancer including colon cancer, endometrial, Ewing's sarcoma, glioblastoma multiforme, hairy cell leukemia, head and neck cancer, Hodgkin's lymphoma, an intraperitoneal tumor, juvenile myelomonocytic leukemia, Kaposi's sarcoma, kidney cancer, liposarcoma, leukemia, lung cancer including advanced and metastatic non-small, lymphoma, malignant pleural effusion, malignant pleural mesothelioma, malignant peritoneal mesothelioma, malignant mesothelioma, mantle cell lymphoma, melanoma, multiple myeloma, myelodysplastic syndrome, neuroblastoma, non-Hodgkin's lymphoma, non-squamous NSCLC, ocular melanoma or retinoblastoma, osteosarcoma, ovarian cancer including relapsed, pancreatic cancer, pediatric sarcoma, peripheral T-cell lymphoma, prostate cancer (including metastatic hormone-refractory prostate cancer), rhabdomyosarcoma, sarcoma, soft tissue sarcoma, spinal cord cancer, squamous cell cancer, stomach cancer, T-cell lymphoma (including relapsed or refractory peripheral), T-cell acute lymphoblastic leukemia, testicular cancer, a trophoblastic neoplasm, and upper gastro-intestinal cancer including esophageal carcinoma, urothelial carcinoma, or Wilms tumor. In further embodiments, the subject has myelodysplastic syndrome (MDS).

In yet further embodiments, the disease, disorder, or condition is inflammation.

In other embodiments, the disease, disorder, or condition is a psychological disorder. In some aspects, the psychological disorder is a psychosis.

In still other embodiments, the disease, disorder, or condition is a dopamine-related disease. Thus, in some aspects, the disease is Parkinson's disease, dopamine-responsive dystonia, restless leg syndrome, amyotrophic lateral sclerosis, or multiple system atrophy. The compounds of Formula (I) or particles containing same may also be used for inhibiting prolactin secretion, stimulating the release of growth hormone, or treating neurological symptoms of chronic manganese intoxications.

An "effective amount" means an amount or dose sufficient to generally bring about the desired therapeutic benefit in patients in need of such treatment for the designated disease, disorder, or condition. Effective amounts or doses of the compounds of Formula (I) or particles containing the compound of Formula (I) may be ascertained by routine methods such as modeling, dose escalation studies or clinical trials, and by taking into consideration routine factors, e.g., the mode or route of administration or drug delivery, the pharmacokinetics of the compound of Formula (I) or biologically active compound, the severity and course of the disease, disorder, or condition, the subject's previous or ongoing therapy, the subject's health status and response to drugs, and the judgment of the treating physician. An example of a dose is in the range of from about 0.001 to about 200 mg of the compound of Formula (I) or biologically active compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In addition, the compounds of Formula (I) or particles containing same may be used in combination with additional active ingredients in the treatment of the above conditions. The additional active ingredients may be co-administered separately with a compound of Formula (I) of the disclosure or included with such an agent in a pharmaceutical composition according to the disclosure. In an exemplary embodiment, additional active ingredients are those that are known or discovered to be effective in the treatment of any of the diseases or disorders described herein. The combination may serve to increase efficacy (e.g., by including in the combination a compound potentiating the potency or effectiveness of an active agent according to the disclosure), decrease one or more side effects, or decrease the required dose of the active agent according to the disclosure.

It is understood that the examples and embodiments described herein are for illustrative purposes only and that various modifications or changes in light thereof will be suggested to persons skilled in the art and are to be included within the spirit and purview of this application and the scope of the appended claims.

EMBODIMENTS

Embodiment 1

A nano-particle comprising a water soluble compound and a hydrophobic chain coupled to the water soluble compound.

Embodiment 2

The nano-particle of Embodiment 1 wherein a linker moiety couples the water soluble compound to the hydrophobic chain.

Embodiment 3

The nano-particle of Embodiment 2 wherein the linker moiety undergoes pH-dependent change in solubility.

Embodiment 4

The nano-particle of Embodiment 2 wherein the linker moiety is pH-labile.

Embodiment 5

The nano-particle of Embodiment 2 wherein the linker moiety undergoes pH-dependent change in solubility and is also pH-labile.

Embodiment 6

The nano-particle of any of Embodiments 2-5 wherein the linker moiety, upon exposure to a target pH, causes the hydrophobic chain to dissociate from the water soluble compound.

Embodiment 7

The nano-particle of Embodiment 6 wherein the target pH is a pH surrounding a tumor environment or lysosmal pH.

Embodiment 8

The nano-particle of Embodiment 1 wherein the water soluble compound is hydrophobic.

Embodiment 9

The nano-particle of Embodiment 1 wherein the water soluble compound is selected from the group consisting of bendamustine, doxorubicin, azacitidine, decitabine, gemcitabine, melphalan, combinations thereof, salts thereof, prodrugs thereof, and derivatives thereof.

Embodiment 10

The nano-particle of Embodiment 1 wherein the nano-particle comprises at least one of a solid lipid nanoparticle, a polymer nanoparticle, a metal nanoparticle, a nanoemulsion, a liposome, or a combination thereof.

Embodiment 11

The nano-particle of Embodiment 10, wherein the nano-particle comprises a polymer nanoparticle.

Embodiment 12

The nano-particle of Embodiment 11, wherein the polymer comprises a diblock copolymer.

Embodiment 13

The nano-particle of Embodiment 12 wherein the diblock copolymer is formed from a hydrophilic block and a hydrophobic block.

EXAMPLES

LC-MS were obtained using an Esquire 2000.
High performance liquid chromatograph (HPLC) was performed using an Agilent 1100.
CEP-40125 refers to dodecyl 4-(5-(bis(2-chloroethyl)amino)-1-methyl-1H-benzo[d]imidazol-2-yl)butanoate having the following structure:

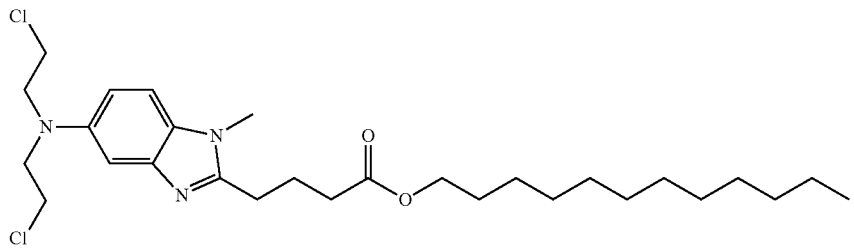 [SMILES: CCCCCCCCCCCCOC(=O)CCCc1nc2cc(N(CCCl)CCCl)ccc2n1C]

CEP-18083 refers to bendamustine hydrochloride, i.e., 2-benzimidazolinebutryric acid, 1-methyl-5-bis(2-chloroethyl)amino-, hydrochloride, having the following structure:

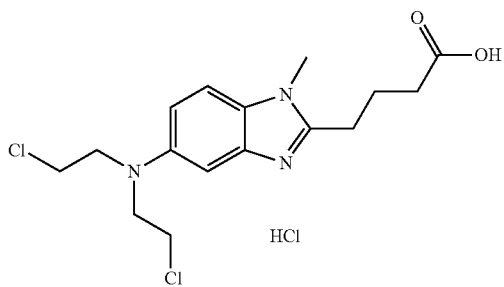 [SMILES: Cn1c(CCCC(=O)O)nc2cc(N(CCCl)CCCl)ccc21 ; Cl]

22Rv1 human prostate carcinoma cells (ATCC®#CRL-2505) were obtained from the American Type Culture Collection (ATCC).

786-0 human renal cell adenocarcinoma cells (ATCC®#CRL-1932) were obtained from the ATCC.

Example 1: Nanoparticles of Prodrug A

Polymer nanoparticle formulations were prepared using a phase inversion technique where polymer and drugs/prodrugs were dissolved in an organic solvent (e.g acetone) and aqueous buffer was slowly added to the organic phase while stirring. Residual solvent from the resulting nanoparticle formulations was removed using tangential flow filtration (TFF). Using Design of Experiments approach, effect of initial drug:polymer ratio, total dissolved solids, polymer type/molecular weight and formulation method (phase inversion vs nanoprecipitation) on the encapsulation efficiency was studied. Formulations were further screened for their in vitro stability by incubation in PBS, rat plasma and by syringe filtration through a 0.2 um filter (to test particle aggregation in high concentration formulations).

Here, a prodrug approach was demonstrated to develop a polymer nanoparticle formulation of a water-soluble drug (log P<2) which undergoes rapid clearance from plasma. Hydrophobic prodrugs of varying fatty acid chain lengths were encapsulated in diblock copolymers and formulations were screened for their encapsulation efficiency, drug loading capacity and in vitro stability.

Why Polymer Nanoparticles?

Polymer properties (e.g. molecular weight, pH responsiveness) can be tuned by synthetic chemistry to alter design features that can be used to control pharmacological outcomes. See, Table 1 and FIG. 1.

TABLE 1

| | Pharmacological outcomes | | | |
|---|---|---|---|---|
| | Localization | | Duration | Total |
| Design Features | Circulation | Tissue/Cellular | of Therapy | Delivered Amount |
| Surface Chemistry | ✓ | ✓ | — | — |
| Responsiveness (e.g. pH triggered release) | ✓ | ✓ | ✓ | ✓ |
| Size | ✓ | ✓ | — | ✓ |
| Loading Capacity | — | — | ✓ | ✓ |
| Degradation | ✓ | ✓ | ✓ | ✓ |

Enhanced Permeation and Retention Effect (EPR Effect)

Figure 2:
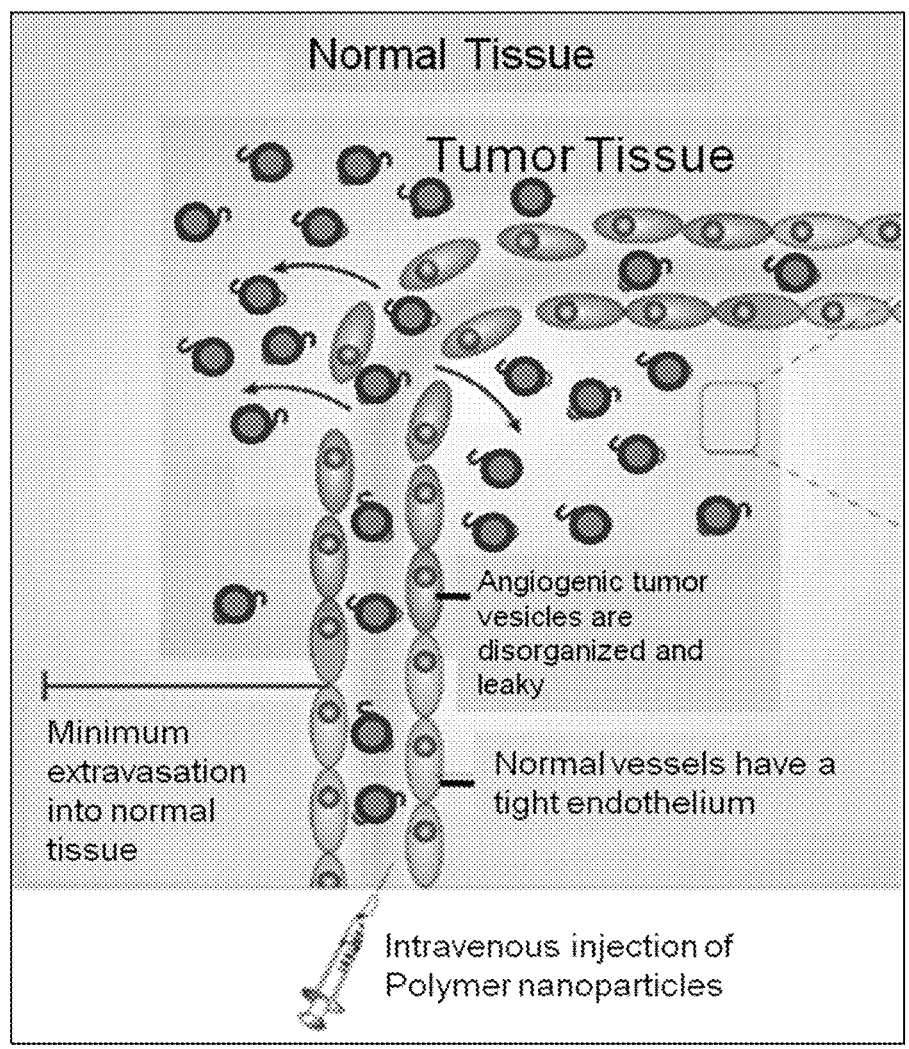
FIG. 2 is a schematic representation of passive tumor targeting of nanoparticles. This figures show intravenous injection of the polymer nanoparticles, the tight endothelium of normal vessel, minimum extravasation into normal tissues, and disorganized and leaky angiogenic tumor vesicles in tumor tissue.

FIG. 2 is a schematic representation of passive tumor targeting of nanoparticles, where particles extravasate only where vasculature is discontinuous and accumulate where lymphatic system is ineffective (i.e. tumor tissue).

Why Prodrugs:

Physical properties of the drugs often limit drug encapsulation efficiency, loading capacity and stability of polymer nanoparticle formulations.

Prodrug approach can be used to tune physical properties of the drug (e.g. convert a lipophobic drug into a lipophilic drug through conjugation to a alkyl chain)

Formulation Methods

1. Phase Inversion

Figure 3:
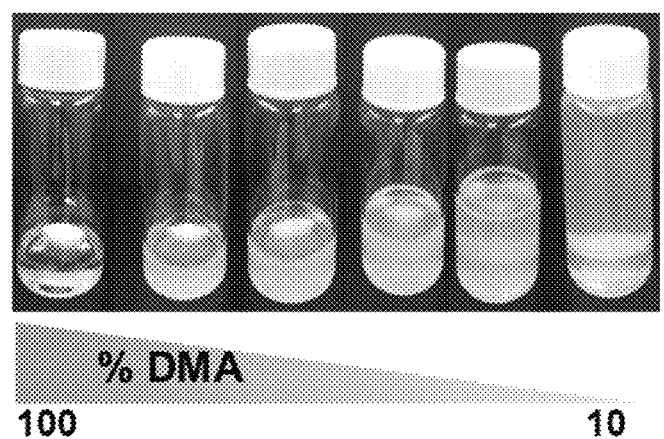
FIG. 3 are images of six vials, containing varying amounts of DMA from 100-0%, of the phase inversion technique of a formulation method described herein.

Diblock copolymer(s) and drug(s) are dissolved in a water miscible organic solvent (e.g. DMA) and water is slowly added to the solution while stirring. See, FIG. 3.

2. Nanoprecipitation

Diblock copolymer(s) and drug(s) are dissolved in a water miscible organic solvent (e.g. DMA). This polymer drug solution is then added to aqueous phase with or without surfactants.

Figure 4:
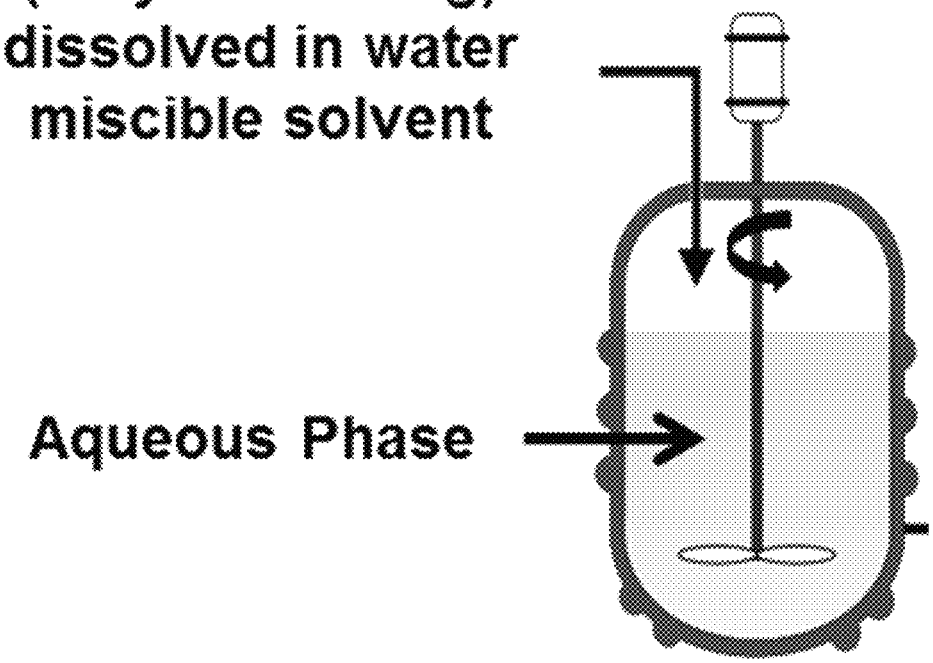
FIG. 4 is a schematic showing a nanoprecipitation formulation method described herein with the addition of a polymer/drug mixture dissolved in water and/or miscible solvent to an aqueous phase.

In all the formulation methods, residual solvent is removed by subjecting nanoparticle suspension to tangential flow filtration (TFF). See, FIG. 4.

Library of Prodrugs and Polymers

Characteristics of the Parent Drug

Highly water soluble, poor aqueous stability, short half-life of circulation. See, Table 2.

Previous attempts to encapsulate the drug in liposomes proved to be very challenging

TABLE 2

| | log P |
|---|---|
| Drug | <2 |
| Prodrug A | 8.5 |
| Prodrug B | 11.8 |

Figure 5:
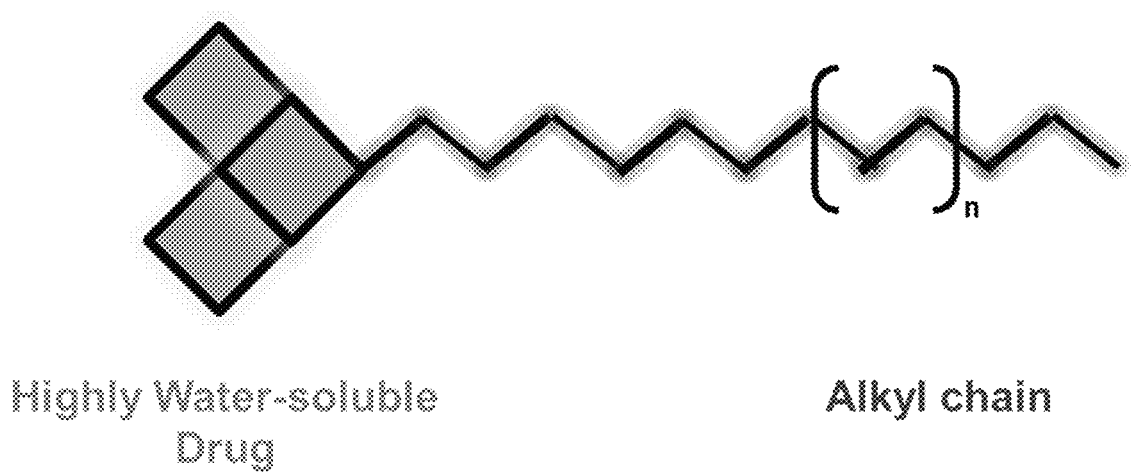
FIG. 5 is a schematic showing the construction of a compound of Formula (I) described herein comprising a highly water-soluble drug and alkyl chain.

Lipophilic prodrugs were synthesized by conjugating the drug to an alkyl chain. FIG. 5. Specifically, Prodrug A (log P 8.5) was encapsulated in $PEG_{2000}$-$PLA_{2000}$ nanoparticles using the procedure described before. 2 ml of nanoparticle suspension was added to 2 ml of diluent. Diluent was either phosphate buffered saline (pH 7.4), 10% human serum albumin (HSA) and mice plasma (pooled). These nanoparticle suspensions were stirred at 37° C. and aliquots were removed periodically and analyzed for concentration of Prodrug A.

A library of prodrugs with varying alkyl chain lengths were synthesized using different linker chemistries.

Combination of prodrugs and polymers were screened to optimize nanoformulations. See, Table 3.

TABLE 3

| Poly(ethylene glycol)-poly(lactic acid) (PELA) | PEG2K-PLA2K |
|---|---|
| | PEG5K-PLA5K |
| | PEG5K-PLA35K |
| | PEG5K-PLA50K |
| Poly(ethylene glycol)-poly(lactic-co-glycolic acid) | PEG5K-PLGA10K |
| | PEG5K-PLGA20K |
| | PEG5K-PLGA55K |
| Poly(ethylene glycol)-poly(caprolactone) | PEG5K-PCL13K |
| | PEG5K-PCL32K |

Nanoparticles of Prodrug A

Using phase inversion method, Prodrug A was encapsulated in poly(ethylene glycol)-b-poly(lactic acid)(PELA) nanoparticles. Specifically, nanoparticle formulations were prepared using the procedure described before or by nanoprecipitation method. Parameters like polymer type/molecular weight, drug:polymer wt %, total dissolved solids (TDS) in organic solvent and solvent can be studied. Formulations were screened for encapsulation efficiency and particle size, before and after filtration through a 0.2 um syringe filter.

Specifically, 200 mg of $PEG_{5000}$-poly(caprolactone)$_{13000}$ [PECL 5-13] and 20 mg of drug were dissolved in 40 ml of acetone [other organic solvents dimethyl acetamide (DMA) or N-methyl-2-pyrrolidone (NMP) could also be used]. Solution was sonicated or warmed as needed to aid dissolution and obtain a clear solution. 4000 ml of phosphate buffered saline (PBS) (pH 7.4) was slowly added to the acetone solution while stirring. Resulting nanoparticle (NP) suspension was subjected to tangential flow filtration to concentrate down to 20 ml. NP suspension was resuspended in 100 ml PBS and concentrated down to 20 ml. This process was repeated one more time. Final NP suspension was filtered through a 0.2 μm PES syringe filter. NP suspension was characterized for particle size and drug concentration.

Figure 7:
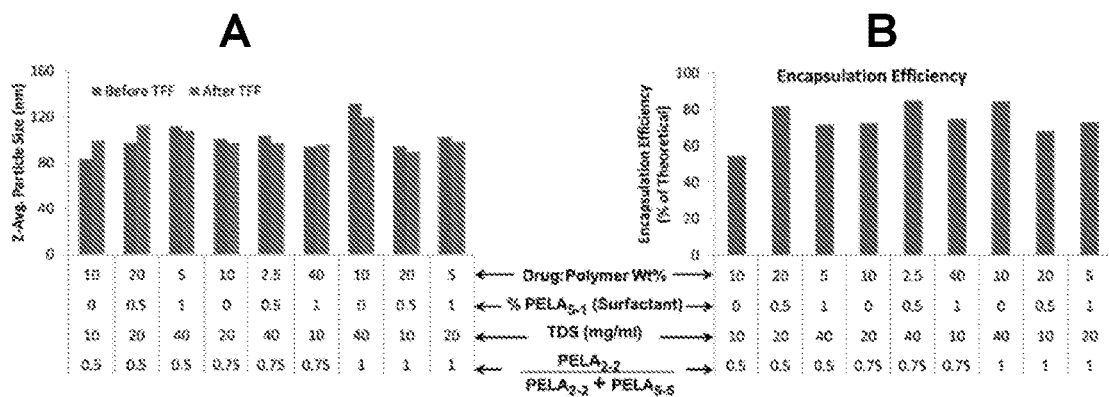
FIG. 7A is a bar graph showing the effects of polymer blend ratio, drug-polymer wt. %, total dissolved solids (TDS), and surface stabilizer (surfactant; % $PELA_{5-1}$) on particle size.
FIG. 7B is a bar graph showing the effects of polymer blend ratio, drug-polymer wt. %, total dissolved solids, and surface stabilizer on encapsulation efficiency.

A DOE was performed to study the effect of polymer blend ratio, drug:polymer wt %, total dissolved solids and surface stabilizer ($PELA_{5-1}$). (FIG. 7)

Figure 6:
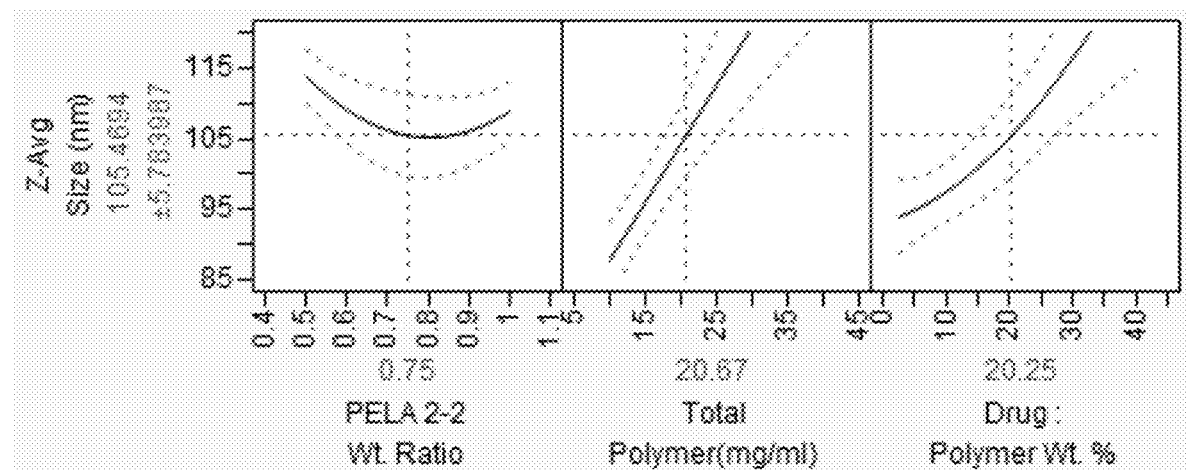
FIG. 6 is a graph showing the particle size and encapsulation efficiency for the nanoparticles of Example 1.

Particle size and encapsulation efficiency were measured. As shown in the profiler graphs in FIG. 6, total dissolved solids and drug:polymer wt % had significant effect on particle size.

A. Stability of Nanoparticle Formulation in Biologically Relevant Media

Figure 8:
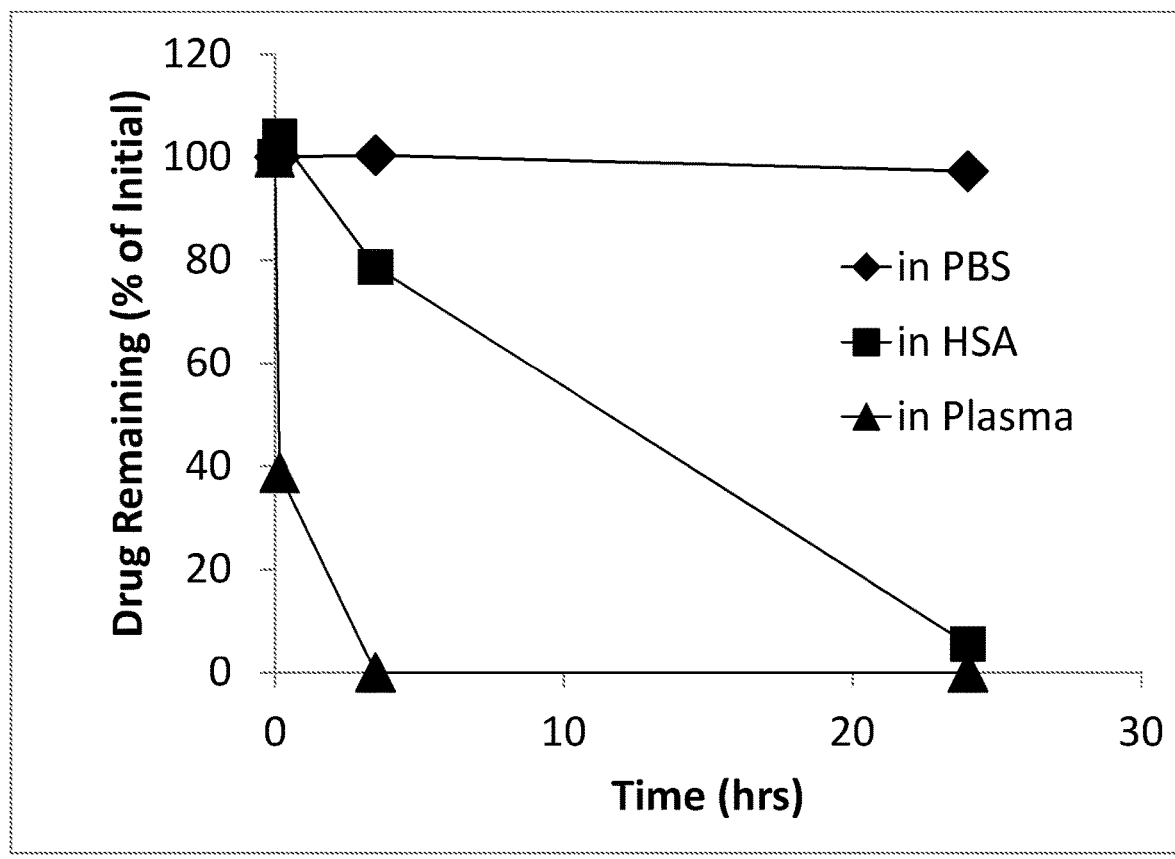
FIG. 8 is a line graph showing the stability of nanoparticle Formulation A of Example 1 in different media, i.e., PBS, HSA, and plasma.

Most of the Prodrug A formulations were stable for over 24 hours in aqueous buffer at pH 7.4. See, FIG. 8 which shows that a nanoparticle formulation that is stable in aqueous buffer resulted in rapid release of the prodrug upon incubation in rat plasma or protein solution.

However, in an in vivo PK study in rodents (IV administration), Prodrug A formulation resulted in a very short circulation half-life where most of the drug accumulated in lungs.

To further investigate this observation, an in vitro study was performed where the Prodrug A nanoformulation was incubated in rat plasma and in a 10% human serum albumin (HSA).

Since the nanoparticles were prepared using low molecular weight diblock copolymers, it was thought that the particles were unstable in the presence of protein.

It was hypothesized that, encapsulating Prodrug A in relatively high molecular weight polymer nanoparticles, would lead to better particle stability in plasma. However, using PEG5K-PLA50K for nanoparticle formulation did not affect release and degradation of drug.

Increasing polymer molecular weight did not affect the rate of release of Prodrug A.

Figure 9:
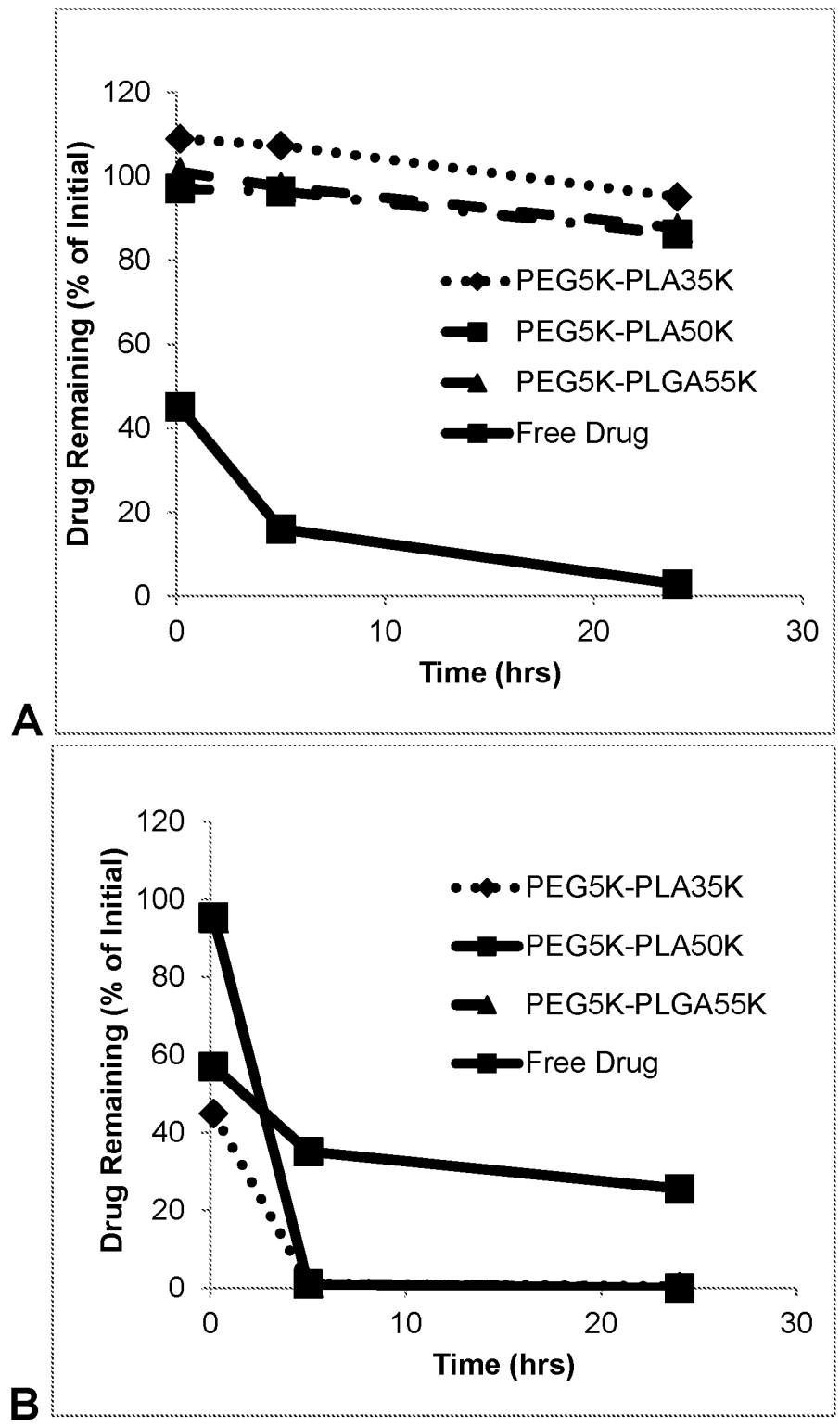
FIG. 9A is a line graph showing the nanoparticle formulation stability in PBS for PEG5K-PLA35K, PEG5K-PLA50K, PEG5K-PLGA55K, and free drug.
FIG. 9B is a line graph showing the nanoparticle formulation stability in rat plasma for PEG5K-PLA35K, PEG5K-PLA50K, PEG5K-PLGA55K, and free drug.

This indicated that, during drug encapsulation by phase inversion, Prodrug A is located at nanoparticle/water interface. When incubated in PBS, drug is insoluble and remains at the nanoparticle interface. However, when incubated in plasma, the proteins in plasma provide "sink" conditions where the drug is released and binds with proteins. Data in FIGS. 9A and 9B demonstrates that using such screening criteria, a long circulating prodrug-polymer nanoparticle formulation was developed with improved tumor accumulation.

B. Optimizing Nanoparticle Formulations—Design of Prodrugs and Screening Criteria Two separate nanoparticle formulations encapsulating Prodrug A (log P 8.5) and Prodrug B (log P 11.8) were prepared using $PEG_{2000}$-$PLA_{2000}$. Two ml of nanoparticle suspension was added to 2 ml of diluent. Diluent was either phosphate buffered saline (pH 7.4), 10% human serum albumin (HSA) and mice or rat plasma (pooled). These nanoparticle suspensions were stirred at 37° C. and aliquots were removed periodically and analyzed for concentration of Prodrug A and Prodrug B.

A library of prodrugs with varying log P values was screened.

Prodrug B, with a log P value of 11.8, was screened with library of polymers and their stability in rat plasma was studied.

Figure 10:
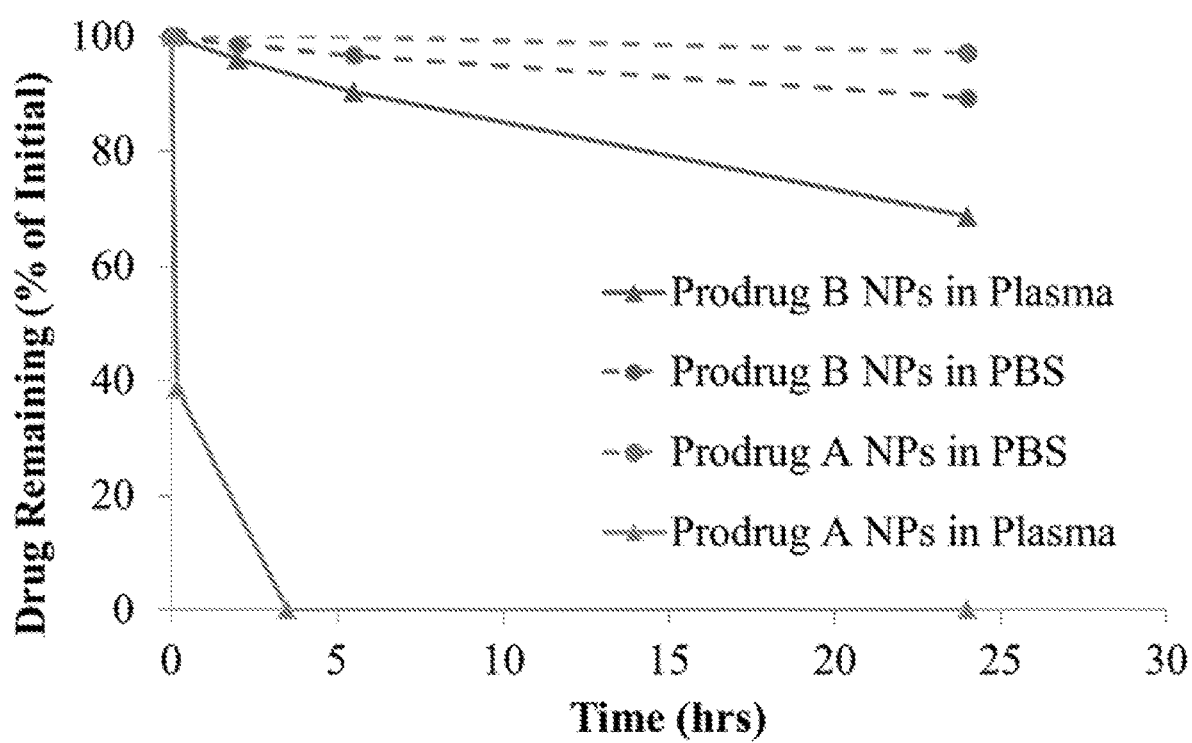
FIG. 10 is a line graph showing the stability of Prodrugs A and B nanoparticles in PBS and plasma.

As compared to Prodrug A, (log P=8.5), nanoparticle formulations of Prodrug B (log P=11.8) were relatively stable in rat plasma where ~70% of encapsulated drug was protected after 24 hrs incubation in plasma at 37° C. See, FIG. 10.

In some cases, IV administration of "optimized" nanoparticle/prodrug formulations in rodents resulted in a very short half-life and poor pharmacokinetic profile for the prodrugs.

Particle size>200 nm could have resulted in nanoparticle/drug accumulation in lungs. In the phase inversion formulation method, it was observed that, during the tangential flow filtration (TFF), particles aggregate and result in increased mean size. (e.g. Particle size before TFF=140 nm, After TFF=220 nm).

Instead of screening formulations before TFF, particle size/encapsulation efficiency/plasma stability were measured after TFF to screen formulations. Also, filtration of nanoparticle formulation through a 0.2 μm filter was added as additional screening criteria.

Figure 11:
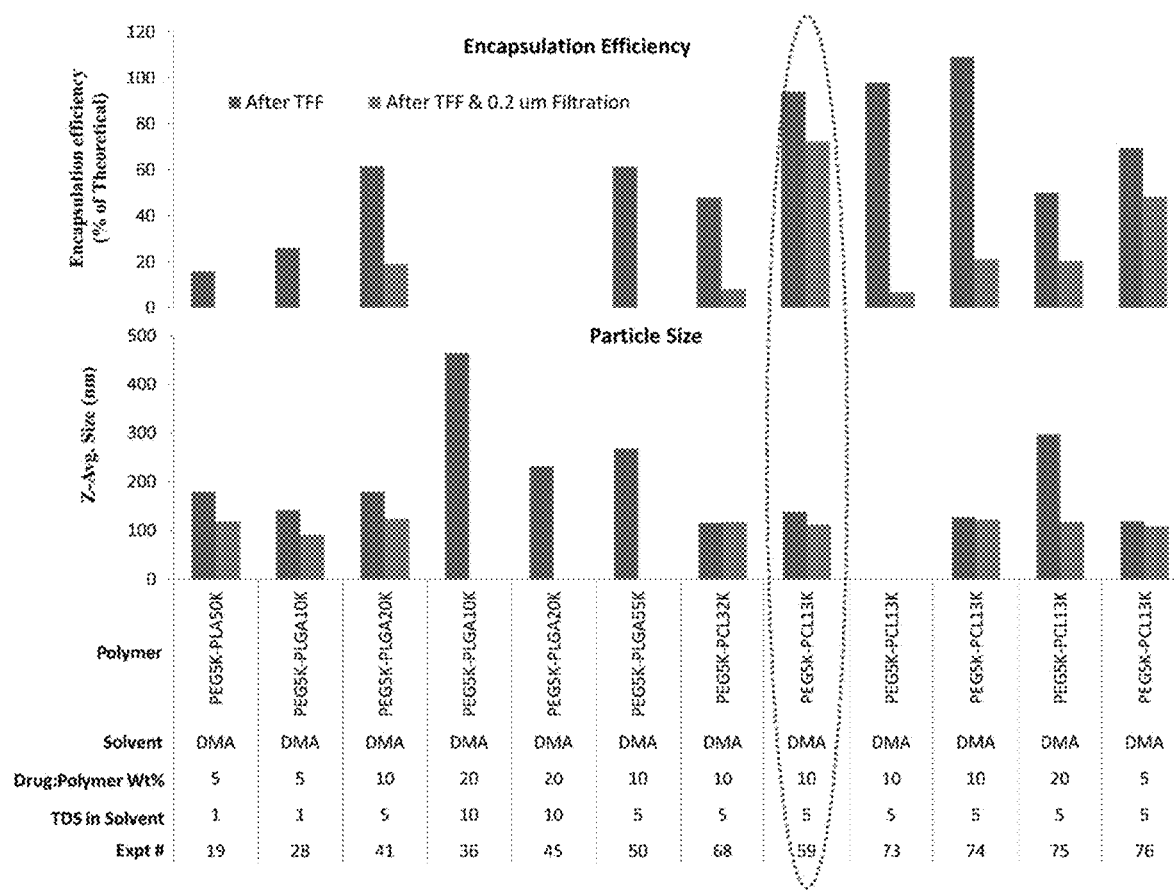
FIG. 11 is a bar graph showing the encapsulation efficiency and particle size of different nanoparticles, i.e., for PEG5K-PLA50K, PEG5K-PLGA10K, PEG5K-PLGA20K, PEG5K-PLGA55K, PEG5K-PLC32K, and PEG5K-PCL13K, at varying drug:polymer wt. % before and after TFF or TFF and 0.2μ filtration.

Using phase inversion method, several different nanoparticles were prepared by varying types of polymer, polymer molecular weight, drug:polymer wt % and total dissolved solids in organic solvent (Dimethyl acetamide). See, FIG. 11.

PEG5K-PCL13K yielded nanoparticles with size<200 nm and encapsulation efficiency of 70% after TFF and 0.2 um filtration.

Nanoparticle of Prodrug A and Prodrug B were administered via tail vein injection to tumor bearing mice.

Figure 12:
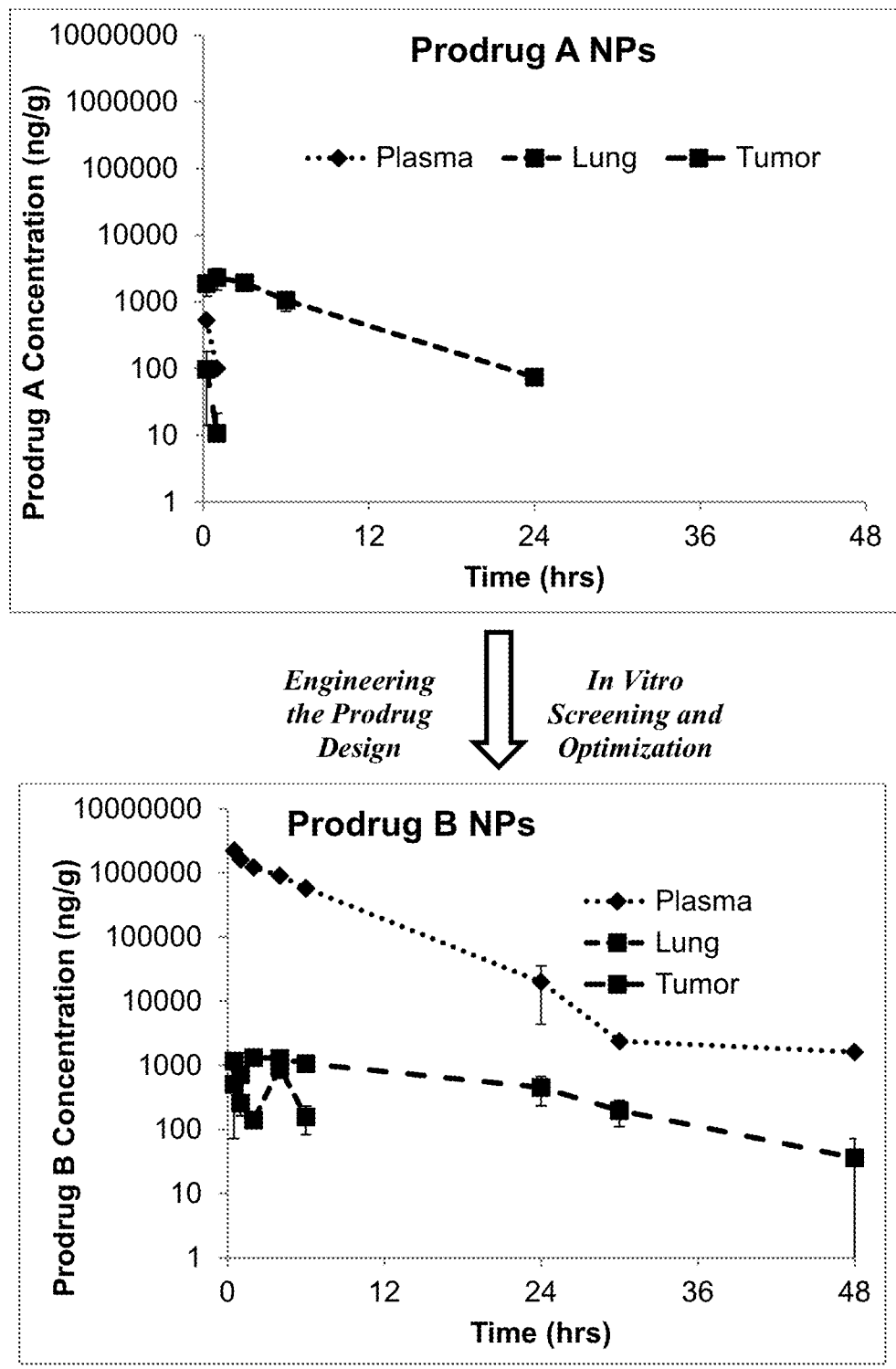
FIG. 12 are line graphs of in vitro screening and optimization comparing the circulation of nanoparticle formulations A and B of Example 1 in plasma, lung, and tumor.

Nanoparticle formulation of Prodrug B formulated using the optimized method resulted in long circulating NPs. See, FIG. 12A-12B.

Conclusions

Nanoparticle formulations designed for parenteral administration should be screened for stability and drug release in biologically relevant media (e.g. plasma or protein solution)

Screening nanoparticle formulations for their filterability through 0.2 μm aided formulation optimization process.

By engineering prodrug design along with thorough in vitro screening methods, a drug was rescued that clears rapidly and made it amenable for the treatment of solid tumors.

Thorough in vitro screening methods aided formulation optimization process resulting in a long circulating polymer nanoparticle formulation.

This data demonstrates the importance of screening nanoparticle formulations for their stability in biologically relevant media. A library of prodrugs (with varying log P values) and polymers were used to prepare nanoparticle formulations that were screened using the criteria mentioned above.

Example 2: General Procedure for Preparing Polymer Nanoparticle Formulations of Lipophilic Prodrugs of the Invention 200 mg of $PEG_{5000}$-poly(caprolactone)$_{13000}$ [PECL 5-13] and 20 mg of drug were dissolved in 40 mL of acetone. Other solvents including dimethylacetamide or N-methyl-2-pyrrolidone may be used. The solution was sonicated or warmed as needed to aid dissolution and obtain a clear solution. Phosphate buffered saline (PBS) (pH 7.4-4000 mL) was slowly added to the acetone solution while stirring. The resulting nanoparticle (NP) suspension was subjected to tangential flow filtration to concentrate down to 20 mL. The NP suspension was resuspended in 100 mL PBS and concentrated down to 20 mL. This process was repeated one more time. The final NP suspension was filtered through a 0.2 μm PES syringe filter. The NP suspension was characterized for particle size and drug concentration.

Example 3: Synthesis of BM1-THP-C18

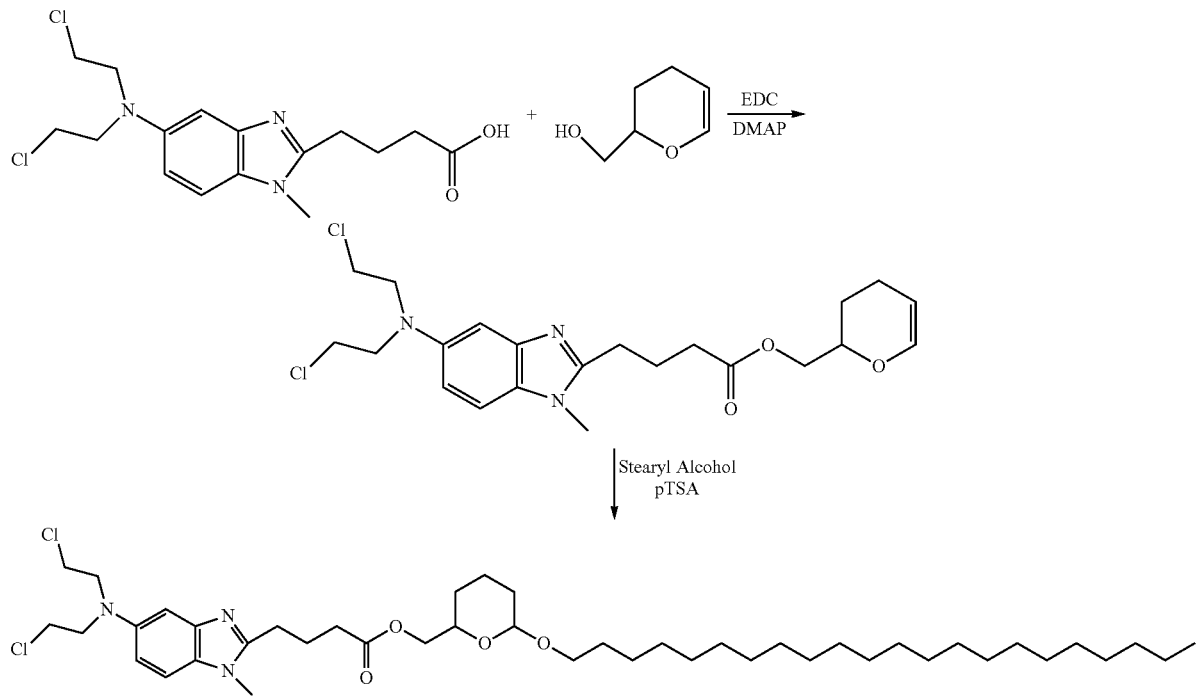

3,4-Dihydro-2H-pyran-2-methanol (DHP-methanol, 1.59 g, 13.95 mmol), 4-dimethylaminopyridine (DMAP, 0.085 g, 0.7 mmol), and 1-ethyl-3-(3-dimethylaminopropyl)carbodiimide (EDC, 2.38 g, 15.35 mmol) were dissolved in 25 mL of dichloromethane (DCM). In a separate flask, bendamustine free base (BM1, 5 g, 13.95 mmol) was weighed and 25 mL of DCM was added to obtain a slurry. This BM1 suspension in DCM was slowly added to DHP-methanol solution. Within 15 minutes, the reaction mixture went completely clear and the reaction was continued for 72 hrs.

Using the DCM:Methanol solvent system, the reaction mixture was analyzed on TLC plates which showed presence of untreated BM1. HPLC analysis of the reaction mixture confirmed the presence of about 30% unreacted BM1. DHP-methanol (0.475 g) and EDC (0.714 g) was added to the reaction mixture and the reaction allowed to proceed overnight.

DCM was evaporated off from the reaction mixture, a small amount of ethyl acetate was added to get everything into solution, and transferred into a 250 mL round bottom flask. Florisil adsorbent was added and mixed well. Ethyl acetate was removed using a rotovap to obtain a smooth flowing florisil adsorbent powder which was packed into a column. Using a DCM:MeOH gradient from 95:5 to 90:10 over 30 mins, the product was separated using a 80 g silica column. The product collected was characterized by LC-MS, HPLC (injection volume: 5 μL, 10-100% MeCN over 5 minutes at 2.5 mL/min) and NMR to confirm molecular weight and purity.

$^1$H NMR of BM1-DHP:

(400 MHz, CHLOROFORM-d) δ 7.18 (d, J=8.8 Hz, 1H), 7.08 (d, J=2.3 Hz, 1H), 6.78 (dd, J=8.8, 2.5 Hz, 1H), 6.41-6.34 (m, 1H), 4.71 (tdd, J=5.4, 2.6, 1.1 Hz, 1H), 4.22-4.12 (m, 2H), 3.76-3.61 (m, 10H), 2.92 (t, J=7.5 Hz, 2H), 2.56 (t, J=7.0 Hz, 2H), 2.30-1.93 (m, 4H), 1.73-1.61 (m, 3H), 1.89-1.58 (m, 1H). BM1-DHP (2.8 g, 6.16 mmol), pyridinium p-toluene sulfonate (PPTS, 0.155 g, 0.616 mol), and p-toluene sulfonic acid (pTSA, 3.7 mmol) were weighed into a round bottom flask and 30 mL of DCM was added. 1-Octadecanol (1.7 g, 6.16 mmol) was weighed and added to the reaction mixture. The reaction mixture slowly went clear. The product was separated by column chromatography by using DCM:MeOH gradient from 100:0 to 95:5. The eluted peak was analyzed by LC-MS (consistent), HPLC (consistent), and NMR for purity.

$^1$H NMR of BM1-THP-C18:

(400 MHz, CHLOROFORM-d) δ 7.17 (d, J=8.8 Hz, 1H), 7.08 (d, J=2.3 Hz, 1H), 6.78 (dd, J=8.8, 2.3 Hz, 1H), 4.82 (s,

1H), 4.17-3.93 (m, 3H), 3.74-3.52 (m, 11H), 2.92 (t, J=7.5 Hz, 2H), 2.58-2.47 (m, 2H), 2.19 (quin, J=7.3 Hz, 2H), 2.04 (s, 1H), 1.90-1.81 (m, 1H), 1.78-1.50 (m, 7H), 1.43-1.33 (m, 2H), 1.31-1.23 (m, 29H), 0.93-0.83 (m, 3H).

Example 4: Synthesis of BM1-THP-Azide-His-C18

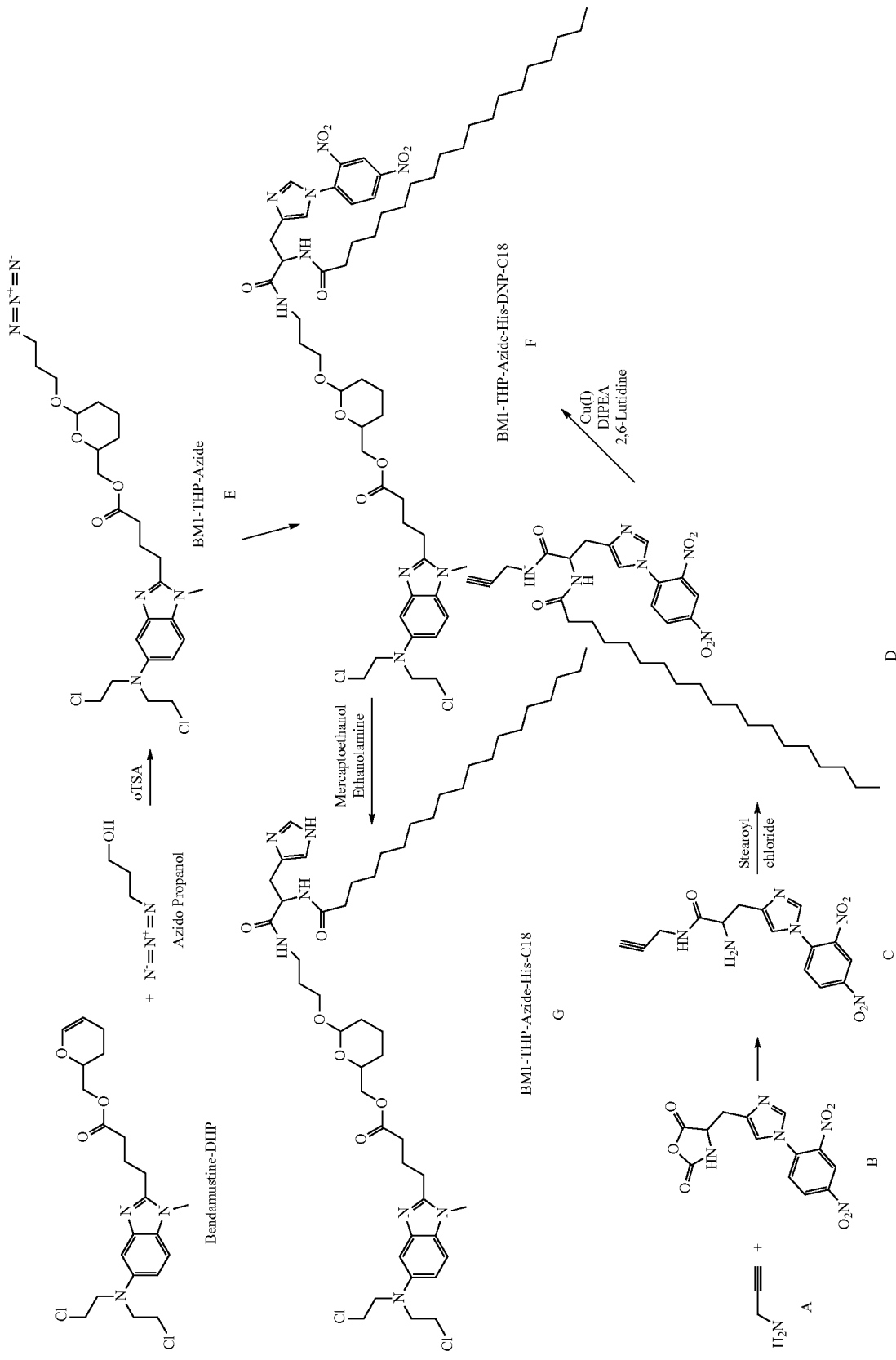

(i) Synthesis of Compound B (DNP-His-NCA)

Boc-His(DNP)-OH.IPA (5.36 g, Product #BH2314, Advanced Chemtech) was weighed in a 50 mL RBF. Anhydrous THF (45 mL) was added and stirred to get a clear solution. To this solution, 3.75 ml of $SOCl_2$ was added dropwise. The solution became turbid and viscous and was stirred for 2 hrs. Anhydrous diethyl ether (450 mL) was added to the reaction mixture and powder was collected by filtration. Filtered powder was washed with additional THF and left overnight under vacuum to remove residual solvents. Product was characterized by LC-MS (consistent) and NMR. $^1$H NMR (400 MHz, DMSO-$d_6$) δ 9.18 (s, 1H), 9.07 (br s, 1H), 9.00 (d, J=2.5 Hz, 1H), 8.80 (dd, J=8.8, 2.8 Hz, 1H), 8.14 (d, J=8.5 Hz, 1H), 7.73 (s, 1H), 4.84 (td, J=6.3, 1.0 Hz, 1H), 3.34-3.15 (m, 2H).

(ii) Synthesis of Compound C (DNP-His-PA)

DNP-His-NCA (1 g, 2.87 mmol) was weighed in a vial and DCM was added. The mixture was sonicated to get a good suspension. While stirring this suspension, 0.9 molar equivalents of trimethylamine ($Et_3N$, 0.261 g, 2.59 mmol) was added and the suspension was immediately filtered to remove trimethylamine hydrochloride salt. In a separate flask, 4 molar equivalents of propargyl amine (PA, 0.64 g, 11.49 mmol) was dissolved in DCM. Filtered DNP-His-NCA solution was slowly added to the propargyl amine solution. The crude reaction mixture was loaded onto the Fluorosil powder and packed into a column. Using 95:5 DCM:methanol with 1% trimethylamine gradient, the desired product was collected. This product solution was washed with DI water to remove excess trimethylamine. The product was characterized by LC-MS (consistent) and NMR.

$^1$H NMR (400 MHz, DMSO-$d_6$) δ 8.95 (d, J=2.5 Hz, 1H), 8.69 (dd, J=8.8, 2.5 Hz, 1H), 8.04-7.97 (m, 2H), 3.90 (br s, 1H), 3.68 (br dd, J=8.0, 5.0 Hz, 2H), 3.11 (t, J=2.5 Hz, 1H), 2.96 (q, J=7.2 Hz, 7H).

(iii) Synthesis of Compound D (DNP-His-PA-C18)

DNP-His-PA (Compound C, 0.48 g) was weighed in a RBF, DCM was added, and an equimolar amount of $Et_3N$ (0.135 g) was added. In a separate vial, equimolar amount of stearoyl chloride (0.406 g) was dissolved in 10 mL of DCM. This stearoyl chloride solution was added dropwise to the DNP-His-PA solution while stirring for 1 hr. Triethylamine hydrochloride salt was filtered out and the reaction mixture was extracted with DI water. DCM was evaporated off to obtain pure product which was characterized by LC-MS (consistent) and NMR.

$^1$H NMR (400 MHz, DMSO-$d_6$) δ 8.93 (d, J=2.5 Hz, 1H), 8.76-8.56 (m, 1H), 8.49-8.23 (m, 1H), 8.11-7.77 (m, 2H), 7.12 (s, 1H), 5.75 (s, 1H), 4.51 (td, J=8.7, 5.3 Hz, 1H), 4.01-3.74 (m, 2H), 3.17-2.62 (m, 3H), 2.36-1.91 (m, 2H), 1.59-0.97 (m, 29H), 0.88-0.83 (m, 3H).

(iv) Synthesis of Compound E (BM1-THP-Azide)

pTSA monohydrate (0.368 g, 1.94 mmol) was weighed in an RBF and 30 mL of toluene was added. While stirring and using a Dan-Stark trap, water was removed from pTSA by heating at 150° C. Residual toluene was removed using vacuum distillation. To this RBF, BM1-DHP (0.4 g, 0.881 mmol) was added and 30 mL of anhydrous DCM was used to dissolve the reagents. While stirring, azido propanol (0.089 g, 0.881 mmol) was added to the solution and the reaction continued for 30 min. The reaction mixture was extracted with $NaHCO_3$ solution. The organic phase was dried over $Na_2SO_4$ and characterized using LC-MS (consistent).

(v) Synthesis of Compound G (BM1-THP-Azide-His-C18)

Anhydrous acetonitrile was bubbled with Ar for 10 min. Compound D (0.675 g, 1.08 mol) and copper iodide (CuI, 20.5 mg, 0.1081 moles) were weighed and added to the acetonitrile. The dispersion was briefly sonicated. 2,6-Lutidine (251.8 µL, 2.16 mmol) and diisopropylethylamine (DIPEA, 376 µL, 2.16 mmol) were added. Compound E (0.6 g, 1.08 mmol) was added at the end and the reaction was continued overnight. To this reaction mixture, 300 µL of mercaptoethanol and 300 µL of ethanolamine were added. The crude reaction mixture was analyzed by LC-MS to monitor the completion of deprotection reaction. The desired product G was isolated by column separation using a 100:0 to 90:10 DCM:methanol gradient. The product was characterized by LC-MS (consistent) and NMR.

$^1$H NMR (400 MHz, DMSO-$d_6$) δ 8.89-8.77 (m, 1H), 8.40-8.29 (m, 1H), 8.02-7.93 (m, 1H), 7.74-7.69 (m, 1H), 7.55 (s, 1H), 7.35-7.29 (m, 1H), 6.91 (d, J=2.3 Hz, 1H), 6.78-6.74 (m, 1H), 5.33 (s, 1H), 4.52-4.22 (m, 4H), 3.70 (s, 6H), 3.67-3.58 (m, 8H), 3.44-3.32 (m, 5H), 3.10-2.98 (m, 3H), 2.82-2.75 (m, 6H), 2.14-1.93 (m, 5H), 1.26-1.16 (m, 34H), 0.89-0.81 (m, 3H).

Example 5: Synthesis of Dox-Hyd-C18

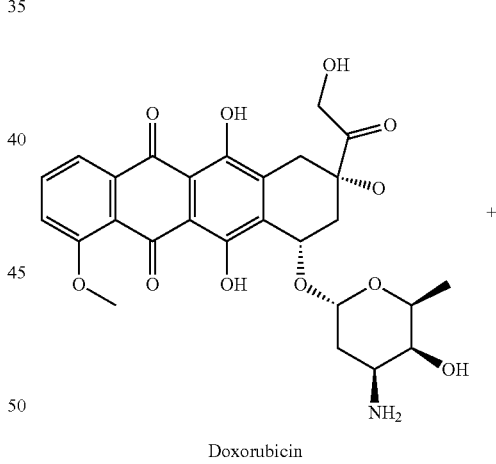

Doxorubicin

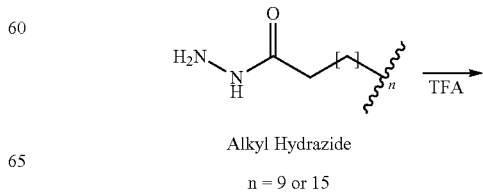

Alkyl Hydrazide n = 9 or 15

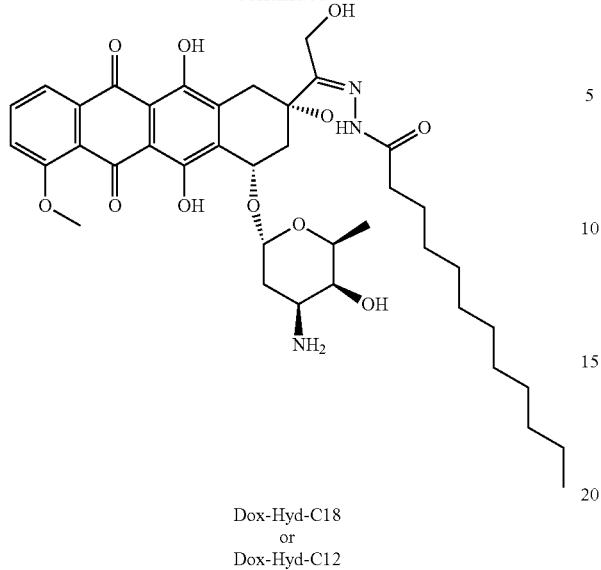

Dox-Hyd-C18
or
Dox-Hyd-C12

Doxorubicin (DOX, 0.25 g, 0.431 mmol), stearic acid hydrazide (0.384 g, 1.28 mmol), pTSA (0.1 g), trifluoroacetic acid (TFA, 150 μL) and activated molecular sieves were added to 100 mL of anhydrous methanol. This solution was warmed to 55° C. and stirred overnight. To remove excess stearic acid hydrazide, 0.5 g of Stratospheres Benzaldehyde resin was added and stirred for 72 hrs. The reaction mixture was then filtered to remove the resin and solvent was removed by vacuum distillation. The product was characterized by LC-MS.

Example 6: Synthesis of CXB-BAE-C18

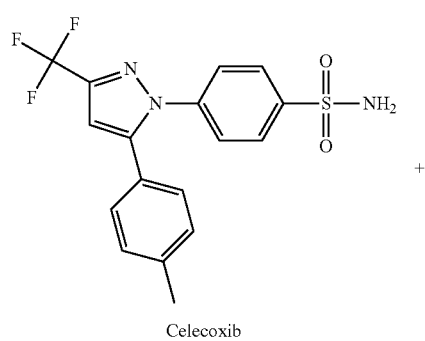

Celecoxib

+

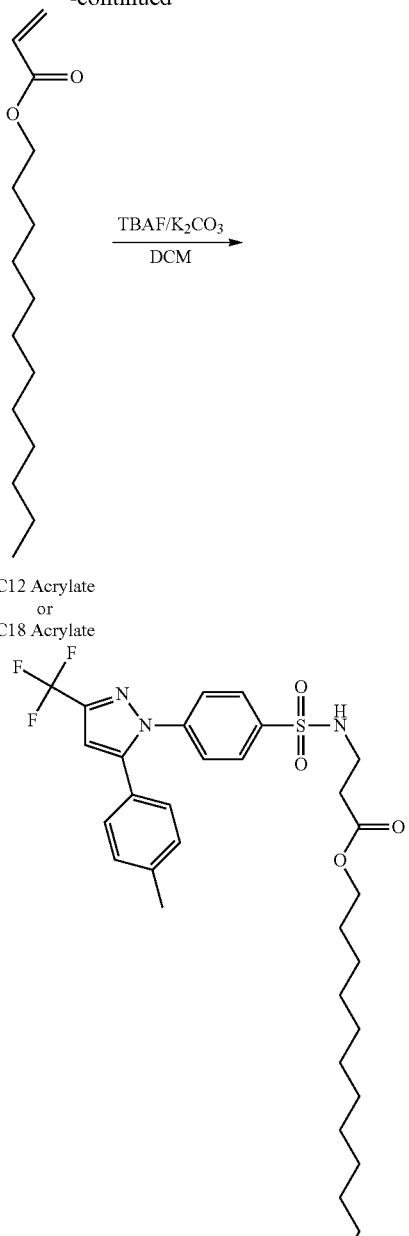

C12 Acrylate
or
C18 Acrylate

CXB-BAE-C12
or
CXB-BAE-C18

Celecoxib (CXB, 1 g), $K_2CO_3$ (0.3623 g), tetrabutylammonium fluoride (TBAF, 0.342 g) and octadecyl acrylate (0.851 g) were weighed and added to a RBF. Anhydrous DCM (35 mL) was added and stirred. The reaction was carried out under reflux conditions at 45° C. for 96 hrs. The reaction mixture was then washed twice with $NaHCO_3$ solution to remove $K_2CO_3$ and TBAF. The DCM phase was dried over $MgSO_4$ and a wax-like product was obtained after vacuum distillation. The product was characterized by LC-MS.

Example 7: Animal Dosing Protocol for PK Studies

IV doses were administered in a fixed dose volume of 100 μL in mice. The mice were sacrificed by decapitation and trunk blood was collected into heparinized tubes at the sampling times stipulated. For blood collection, each rat (unanesthetized) was placed in a clear Plexiglas® restraining tube, and blood samples (approximately 0.25 mL) were drawn from a lateral tail vein into heparinized collection tubes at the sampling times stipulated. (Note: No pre-dose samples were obtained.) The blood samples were placed on wet ice until centrifuged to separate plasma. The plasma fraction was transferred into clean, dry tubes, frozen on dry ice and stored at approximately −20° C. pending analysis. Highly perfused organs (liver, lung) were rapidly removed at the predetermined time points and frozen on dry ice. All tissue samples were also stored at approximately −20° C. pending analysis.

The plasma concentration data for all mice and rats were entered into Excel spreadsheets in preparation for pharmacokinetic analysis. Mean pharmacokinetic parameters were estimated by non-compartmental analysis (Gibaldi and Perrier 1982) of the plasma concentration versus time data using WinNonlin software (Professional Version 4.1, Pharsight Corporation, Palo Alto, Calif.). The terminal rate constant for elimination from plasma (β) was estimated by linear regression of the terminal portion of the semi-logarithmic plasma concentration versus time curve. The apparent terminal half-life ($t_{1/2}$) was calculated as 0.693 divided by β. The area under the plasma concentration versus time curve from time zero to the time of the last measurable concentration ($AUC_{0-t}$) after a single dose was determined by the linear trapezoidal rule. The area from zero to infinity ($AUC_{0-\infty}$) was calculated as the sum of $AUC_{0-t}$ and the area extrapolated from the last measurable concentration to infinity (Clast/β). Concentrations pre-dose were all assumed to be zero for the purpose of calculation of the AUC. Any concentration that was below the limit of quantification (BLQ) after the last quantifiable sampling time was considered to be an empty value for the purpose of calculation of the AUC; it was treated as zero for the calculation of the mean concentration for a given sampling time.

Example 8: pH Sensitive Bendamustine Prodrug

BM1-THP-C12 and BM1-THP-C18 were prepared as described in Example 3. These prodrugs were dissolved in dimethyl acetamide (DMA) and then mixed with Solutol HS 15. This solution was diluted in water to obtain a liquid formulation (29.2 vol % Solutol HS 15, 5.8 vol % DMA and 65 vol % water/buffer). The concentration of prodrug in this liquid formulation was about 0.16 to 1.6 mg/ml. This liquid formulation was then diluted in dissolution media of choice to test stability. Aliquots were removed at various time points and analyzed to determine concentration of prodrug.

The rates of degradation of BM1-THP-C12, BM1-THP-C18, and CEP40125 were, independently, tested in PBS, PBS with pTSA, and methanol with pTSA. It was found that BM1-THP-C18 was insoluble enough to protect pH-sensitive THP group from aqueous environment. BM1-THP-C12 behaved very similarly to CEP-40125.

Specifically, the data showed in vitro hydrolysis of BM1-THP-C18 prodrug at acidic pH in methanol. The prodrug was insoluble in water and hence methanol was used solubilize the prodrug for this hydrolysis experiment. See, Table 4.

TABLE 4

|  |  |  | AUC @ t (h) | | |
|---|---|---|---|---|---|
|  | Dissolution Media | pH | 0 | 3 | 18 |
| BM1-THP-C18 | PBS | 7.4 | 739 | 737 | 703 |
| Liquid | PBS with pTSA | 1 | 743 | 732 | 709 |
| Formulation | Methanol with pTSA | 1 | 740 | — | 0 |

Example 9: BM1-THP-C18 Encapsulated in Nanoparticles—PK Data

In this example, BM1-THP-C18 was encapsulated in polymer nanoparticles as described above and dosed as 1.38 mg-eq/kg to nude mice having 22Rv1-positive tumors as outlined in Example 7. CEP-18083 was independently administered to mice. Conversion to bendamustine was measured in plasma and tumor cells. See, Table 5.

TABLE 5

| 1.38 mg-eq/kg, IV | BM1-THP-C18 | CEP-18083 | BM1-THP-C18 | CEP-18083 |
|---|---|---|---|---|
| $C_{max}$ (ng/mL) | 48350 | 132 | 2619 | 92 |
| $AUC_{0-t}$ (ng · h/mL) | 186019 | 695 | 11964 | 444 |
| Mean n = 2, nude mice | Plasma | | Tumor | |

Figure 13:
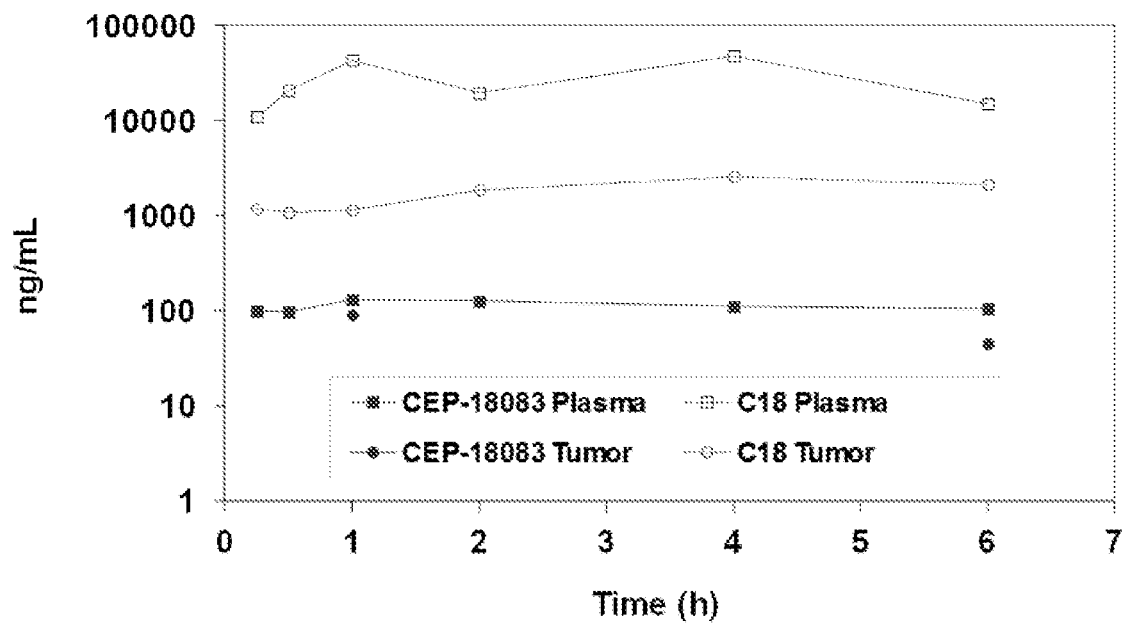
FIG. 13 is a plot of plasma levels of CEP-18083 and BM1-THP-C18 dosed as 1.38 mg-eq/kg IV BM-THP-C18 in nude mice.

The in vivo tumor PK data showed conversion of BM1-THP-C18 to free BM1, which was at low levels. See, FIG. 13.

Example 10: Nanoparticles of BM1-THP-C18-PK Data

In this example, BM1-THP-C18 was encapsulated in polymer nanoparticles as described above and dosed to SCID mice (average weight=20 grams) having 786-0 human renal cell adenocarcinoma tumors and the pharmacokinetics monitored for 48 hours. See, Table 6.

TABLE 6

| 1.37 mg-eq/kg, IV | BM1-THP-C18 | 63 nM NPs | BM1-THP-C18 | Bendamustine | Bendamustine |
|---|---|---|---|---|---|
| $t_{1/2}$ (h) | 4.2 | $C_{max}$ (ng/mL) | 1320 | 421 | 36 |
| $AUC_{0-t}$ (ng · h/mL) | 12794885 | $t_{max}$ (h) | 2 | 0.5 | 2 |
| $AUC_{0-\infty}$ (ng · h/mL) | 12804520 | $AUC_{0-t}$ (ng · h/mL) | 24410 | 3942 | 36 |
| Vd (L/kg) | 0.002 | $AUC_{0-\infty}$ (ng · h/mL) | 24760 | 4070 | ND |
| CL (mL/min//kg) | 0.005 | $t_{1/2}$ (h) | 6.7 | 4.9 | ND |
| Female SCID Mice | Plasma | | Tumor | Plasma | Tumor |

The results showed that the prodrug was accumulating in the tumor but the levels of free bendamustine were low. It is hypothesized that the low conversion to free bendamustine could be due to that the prodrug is so water-insoluble that it is still trapped in the nanoparticle which has accumulated in the tumor tissue.

Example 11: Nanoparticles of BM1-THP-Az-His-C18

BM1-THP-Az-His-C18 was prepared as described in Example 4 and encapsulated in polymer nanoparticles. The particle size was then measured before and after filtration using a 0.2 μm filter.

TABLE 7

| Sample | Actual Conc. (mg/ml) | Mass of Drug (mg) | Encapsulation Efficiency (%) | Z-avg Particle Size (nm) |
|---|---|---|---|---|
| before 0.2 μm filtration | 0.86 | 17.3 | 57.61312 | 67 |
| after 0.2 μm filtration | 0.83 | 16.6 | 55.49 | 64 |

These data shows that particle size did not change significantly after 0.2 μm filtration.

Example 12: Nanoparticles of BM1-THP-Az-His-C18-PK Data

In this example, BM1-THP-Az-His-C18 was encapsulated in polymer nanoparticles as described above and dosed at 1.2 mg-eq/kg to SCID mice (average weight=25 grams) as described in Example 7 and the pharmacokinetics monitored for 48 hours. See, Table 8.

TABLE 8

| 1.2 mg-eq/kg, IV | BM1-THP-Azide-C18 | 63 nM NPs | Bendamustine |
|---|---|---|---|
| $t_{1/2}$ (h) | ND | $C_{max}$ (ng/mL) | 1660 |
| $AUC_{0-t}$ (ng · h/mL) | ND | $t_{max}$ (h) | 0083 |
| $AUC_{0-\infty}$ (ng · h/mL) | ND | $AUC_{0-t}$ (ng · h/mL) | 566 |
| Vd (L/kg) | ND | $AUC_{0-\infty}$ (ng · h/mL) | 589 |
| CL (mL/min//kg) | ND | $t_{1/2}$ (h) | 0.7 |
| Female SCID Mice | Plasma | | Tumor |

Figure 14:
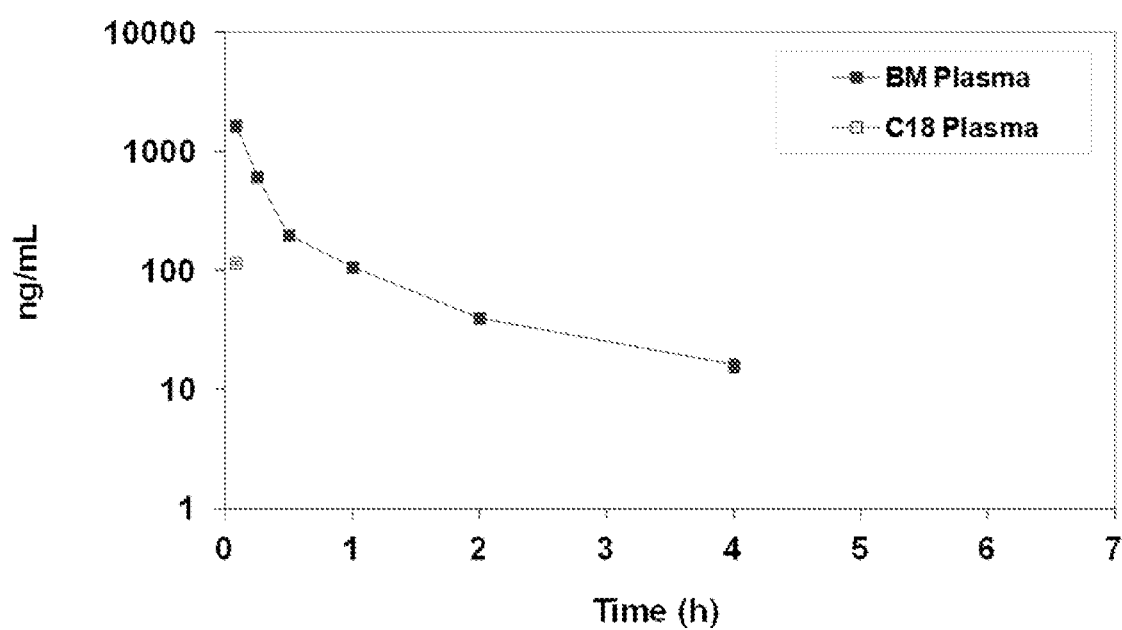
FIG. 14 is a plot of plasma levels of BM and BM-C18 in SCID mice dosed as 1.2 mg-eq/kg IV of BM-THP-Azide-His-C18 NP.

See, FIG. 14. These results show that the nanoparticle formulation for BM1-THP-Az-His-C18 was not optimized before the study. Poor circulation of nanoparticles may have resulted in short half-life of the prodrug.

Example 13: Nanoparticles of BM1-THP-Az-His-C18-PK Data

In this example, BM1-THP-Az-His-C18 was encapsulated in polymer nanoparticles as described above and dosed at 1.2 mg-eq/kg to SCID mice (average weight=25 grams) as described in Example 7 and the pharmacokinetics and levels in liver and lung tissues measured. See, Table 8.

TABLE 9

| 1.2 mg-eq/kg, IV | BM1-THP-Azide-His-C18 | Bendamustine | BM1-THP-Azide-His-C18 | Bendamustine |
|---|---|---|---|---|
| $C_{max}$ (ng/mL) | 6890 | 109 | 806 | 155 |
| $t_{max}$ (h) | 0.083 | 0.083 | 0.083 | 0.083 |
| $AUC_{0-t}$ (ng · h/mL) | 3777 | 32 | 419 | 38 |
| $AUC_{0-\infty}$ (ng · h/mL) | 3863 | ND | 646 | ND |
| $t_{1/2}$ (h) | 1.3 | ND | 1.3 | ND |
| 64 nM NPs | Liver | | Lung | |

This data shows that the prodrug was converted to free drug in lung and liver tissues, although at low levels.

Example 14: DOX-Hyd-C18 in Nanoparticles—PK Data

Figure 15:
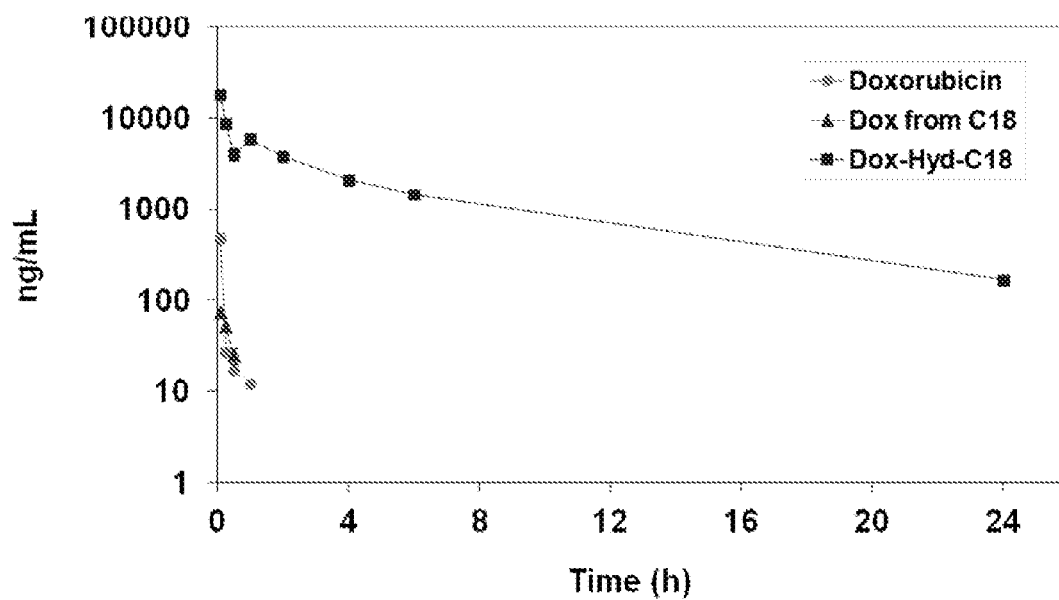
FIG. 15A is a line graph of plasma levels of doxorubicin and Dox-Hyd-C18 at about 1.8 mg/kg or eq IV in female SCID mice
FIG. 15B is a line graph of liver levels of doxorubicin and Dox-Hyd-C18 at about 1.8 mg/kg or eq IV in female SCID mice
FIG. 15C is a line graph of lung levels of doxorubicin and Dox-Hyd-C18 at about 1.8 mg/kg or eq IV in female SCID mice
Figure 15:
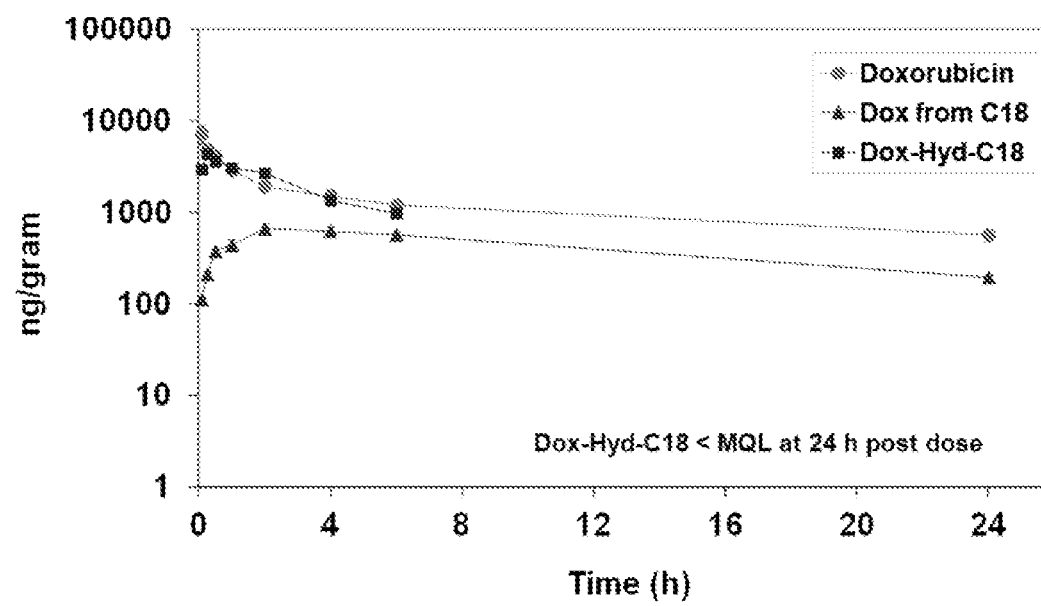
Figure 15:
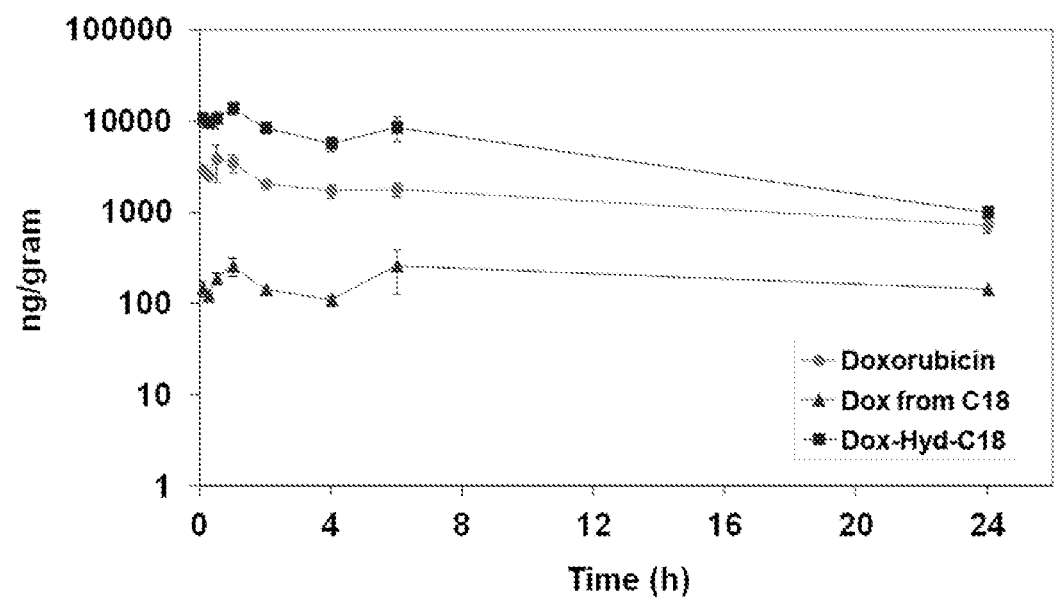

In this example, Dox-Hyd-C18 was encapsulated in polymer nanoparticles as described above and dosed at about 1.8 mg-eq/kg to female SCID mice (average weight=25 grams) as described in Example 7 and the levels in plasma, liver, and lung tissues measured. See, FIGS. 15A-15C.

These data illustrate that the Dox-Hyd-C18 nanoparticles circulate in plasma for up to 24 hours. Further, doxorubicin from hydrolysis of Dox-Hyd-C18 was detected in liver and lung tissue.

Example 15: DOX-Hyd-C12 in Nanoparticles—PK Data

Figure 16:
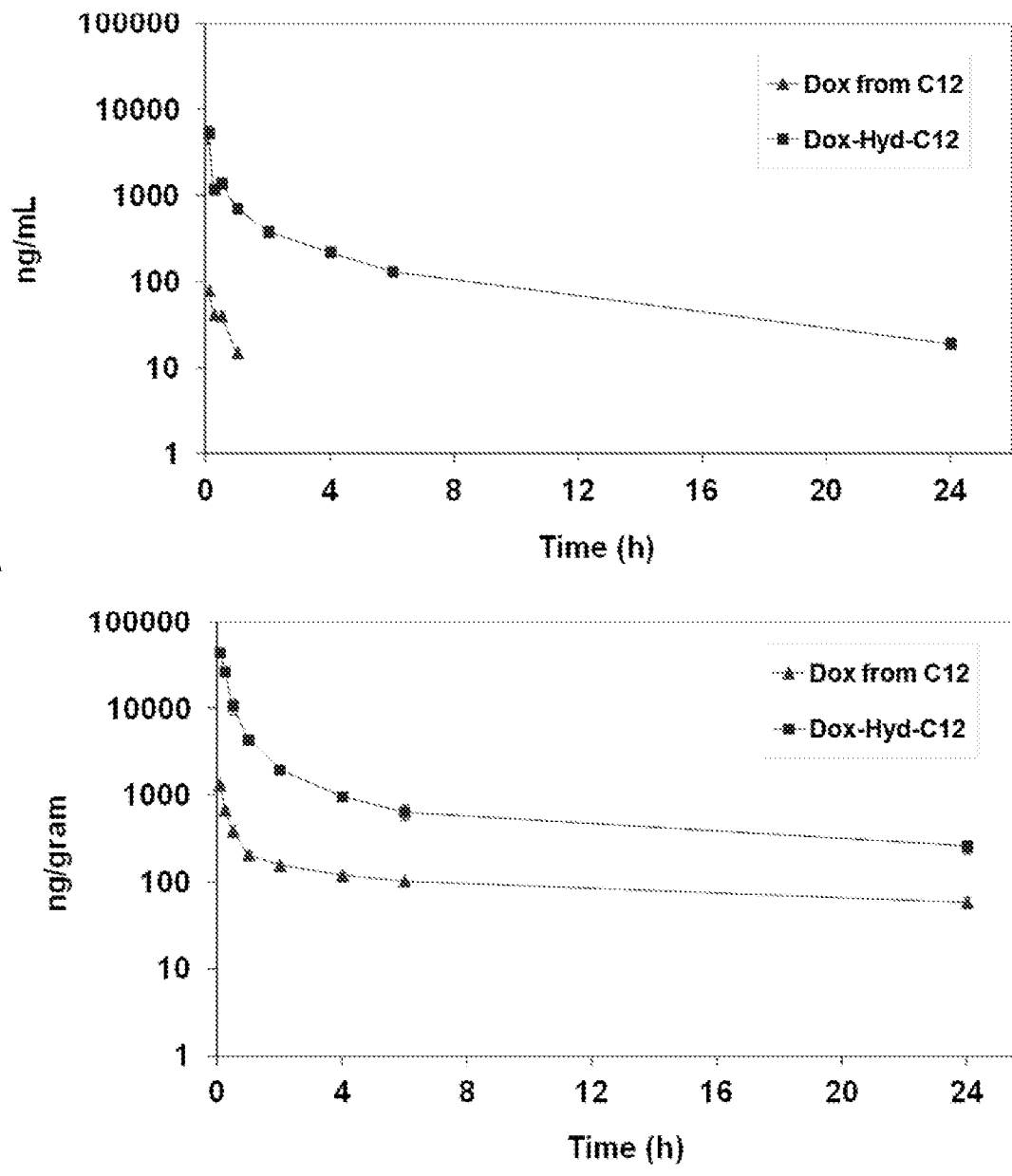
FIG. 16A is a line graph of plasma levels of doxorubicin and Dox-Hyd-C12 at 22 mg-eq/kg IV in female SCID mice.
FIG. 16B is a line graph of liver levels of doxorubicin and Dox-Hyd-C12 at 22 mg-eq/kg IV in female SCID mice.
FIG. 16C is a line graph of lung levels of doxorubicin and Dox-Hyd-C12 at 22 mg-eq/kg IV in female SCID mice.
Figure 16:
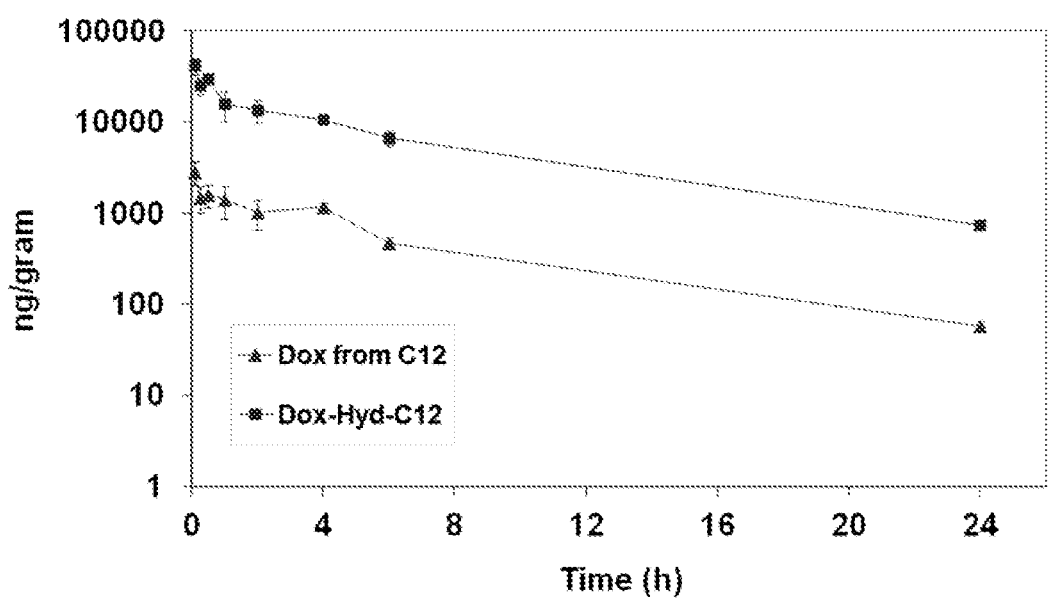

In this example, Dox-Hyd-C12 was encapsulated in polymer nanoparticles as described above and dosed at about 2.2 mg-eq/kg to female SCID mice (average weight=25 grams) as described in Example 7 and the levels in plasma, liver, and lung tissues measured. See, FIGS. 16A-16C.

These data illustrate that Dox-Hyd-C12 nanoparticles circulate in plasma for up to 24 hours. Further, doxorubicin from hydrolysis of Dox-Hyd-C18 was detected in liver and lung tissue.

Example 16: In Vitro Hydrolysis Studies of CXB Prodrugs

Figure 17:
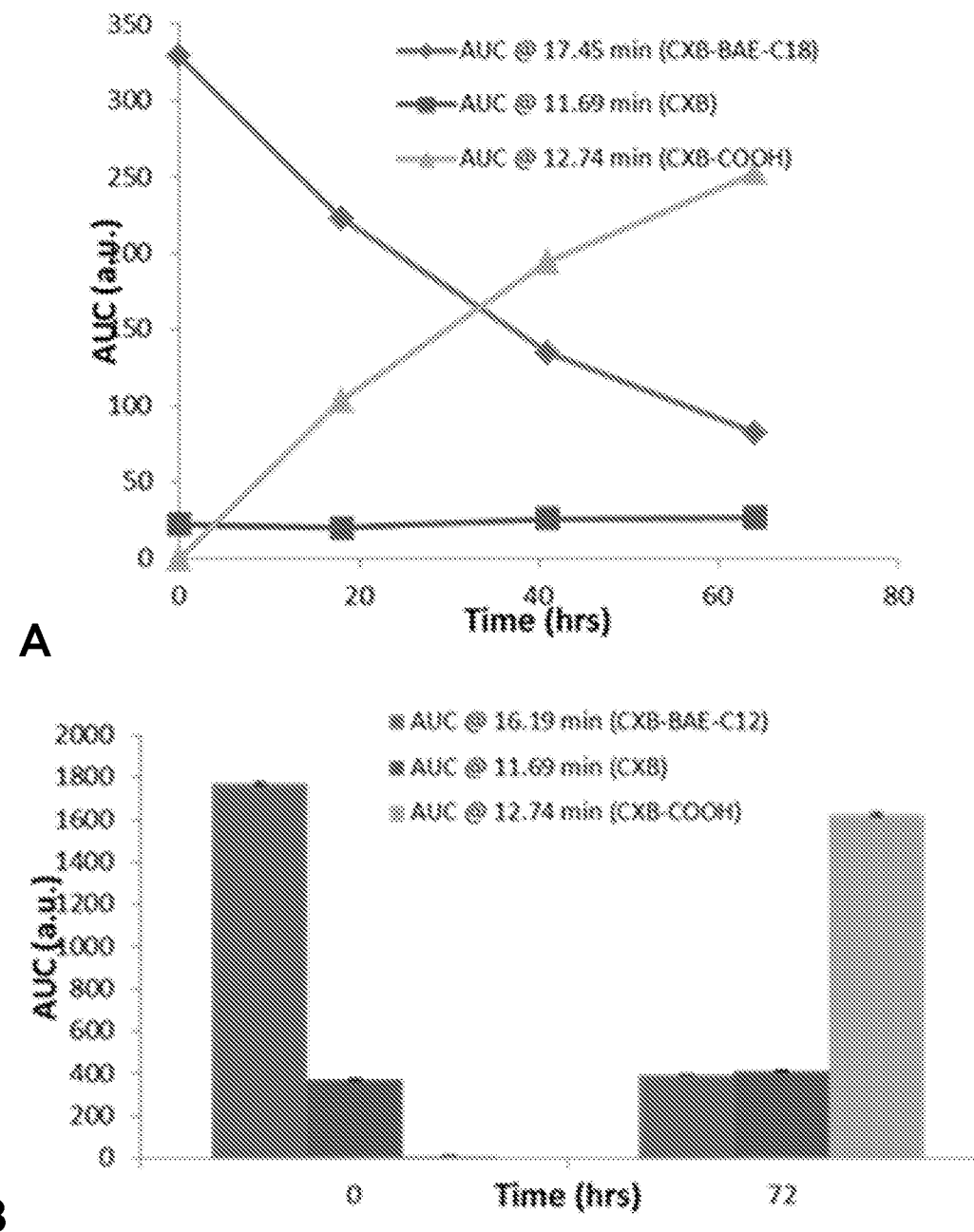
FIG. 17A is line graph showing the hydrolysis of CXB-BAE-C18 in rat plasma.
FIG. 17B is a bar graph showing the hydrolysis of CXB-BAE-C12 in acidic MeOH.
FIG. 17C is a line graph showing the hydrolysis of CXB-BAE-C18 in acidic MeOH.
Figure 17:
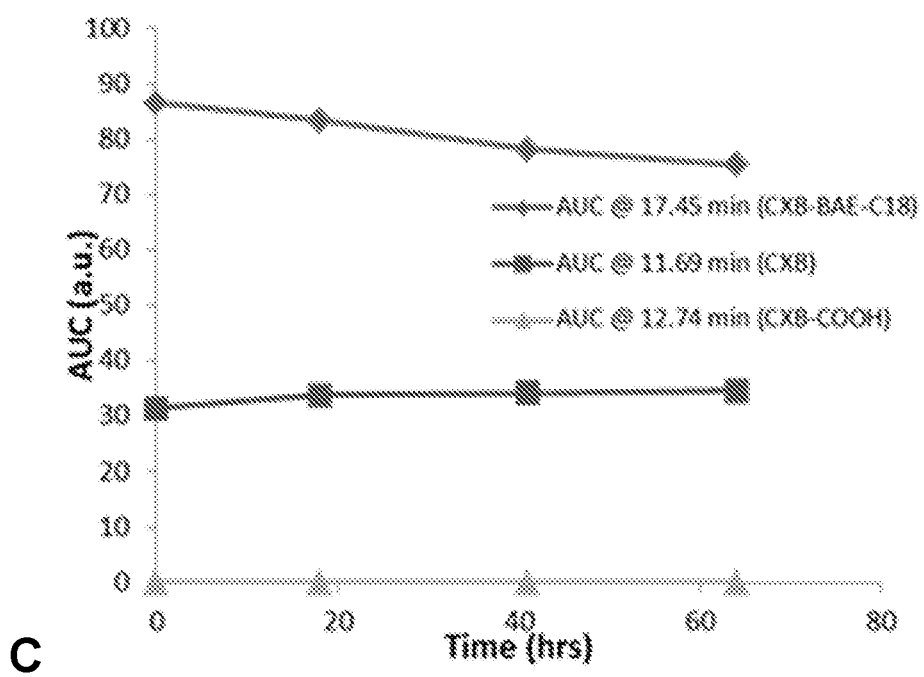

CXB-BAE-C18 was prepared as described in Example 6 and its hydrolysis measured in acidic methanol. See. FIGS. 17A-17B which show that at acidic pH, CXB-BAE-C18 degrades over time to release CXB-COOH which is the hydrolysis product.

The hydrolysis of CXB-BAE-C18 was then measured in rat plasma. See, FIG. 17C which shows that the rate of hydrolysis of CXB-BAE-C18 plasma is much lower compared to acidic methanol.

Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

What is claimed is:
1. Particles comprising one or more compounds that are:
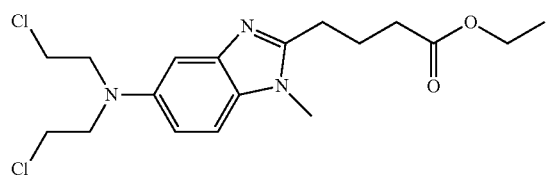
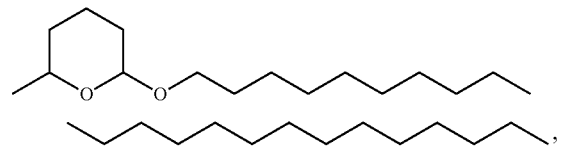
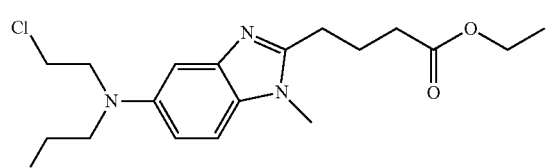
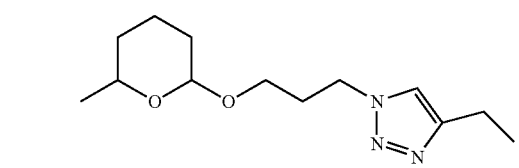
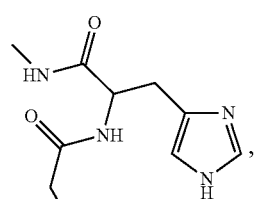
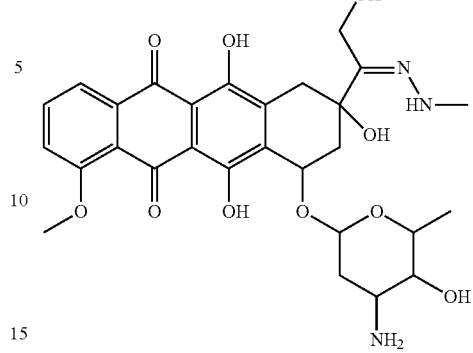
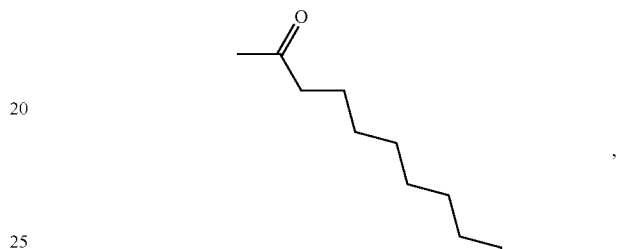
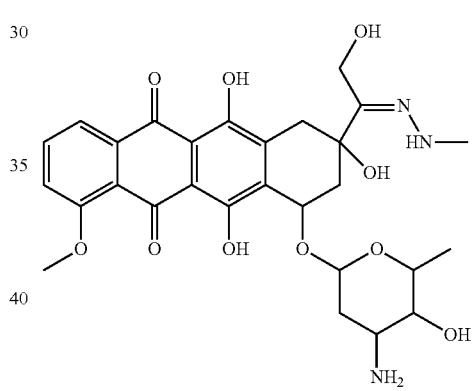
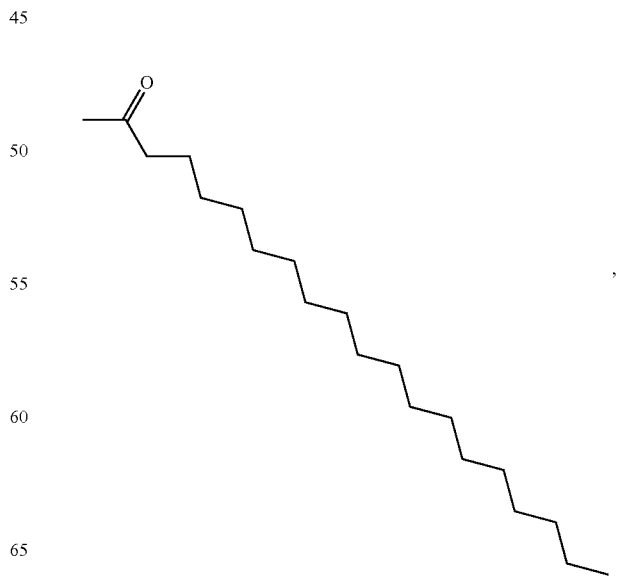

-continued
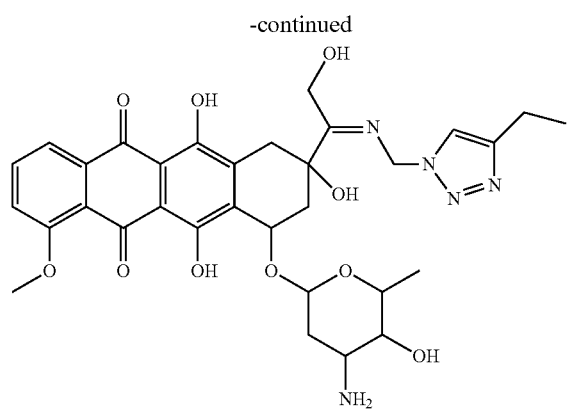
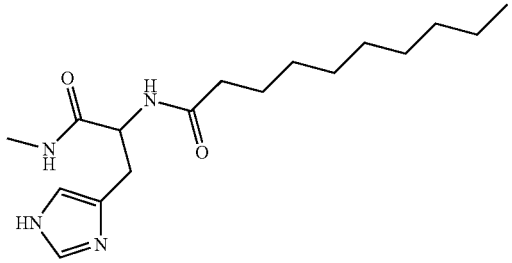
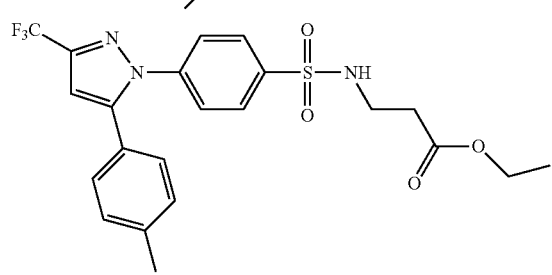
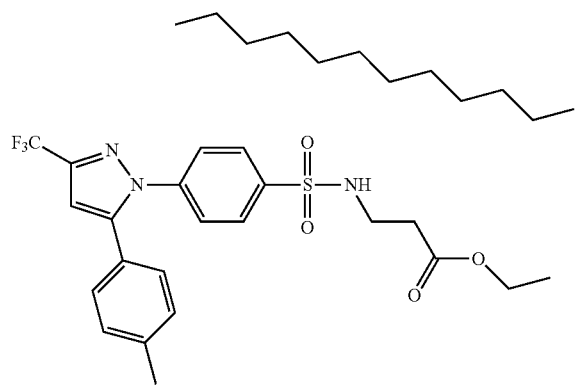
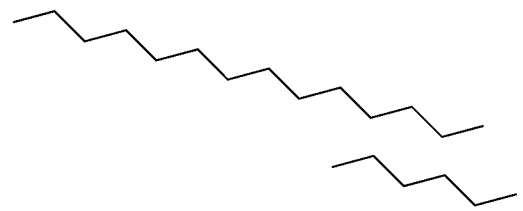
-continued
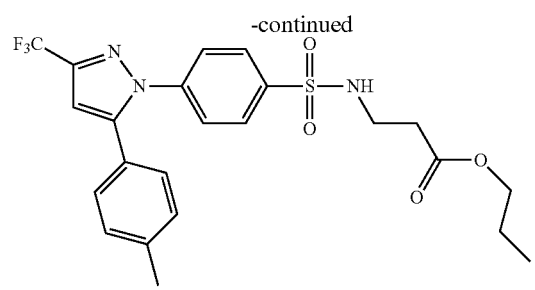
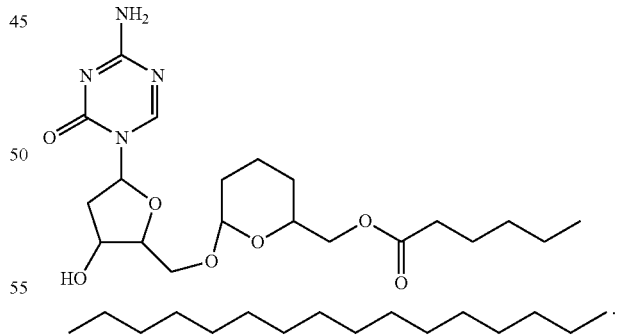
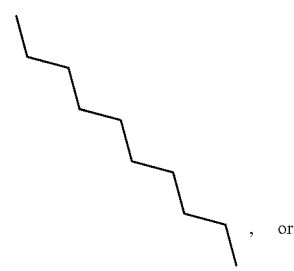
, or
2. The particles of claim 1, which are nano-particles or microparticles.
3. The particles of claim 2, further comprising a diblock or triblock copolymer.
4. A composition comprising the particles of claim 1 and a pharmaceutically acceptable carrier.
5. The composition of claim 4 in the form of a suspension, emulsion, dispersion, or depot.

6. Particles comprising one or more compounds that are:
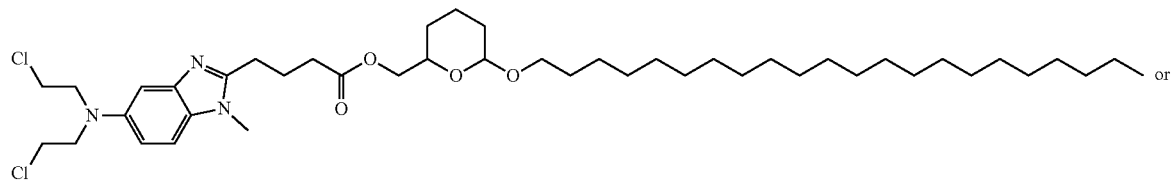
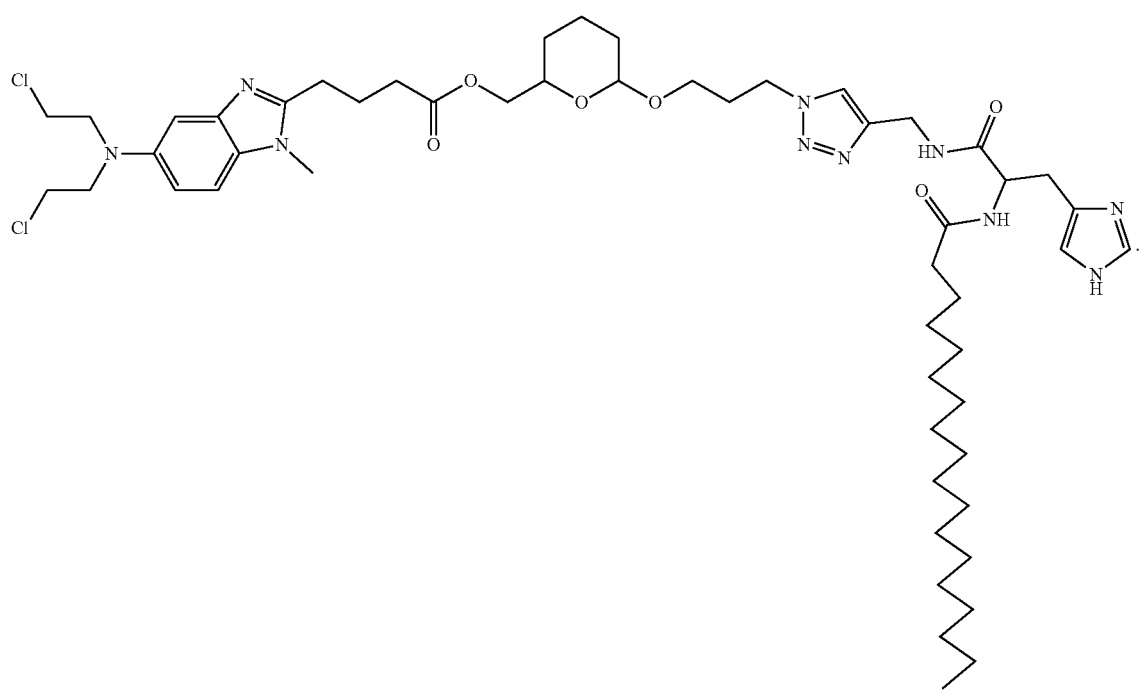
7. Particles comprising one or more compounds that are:
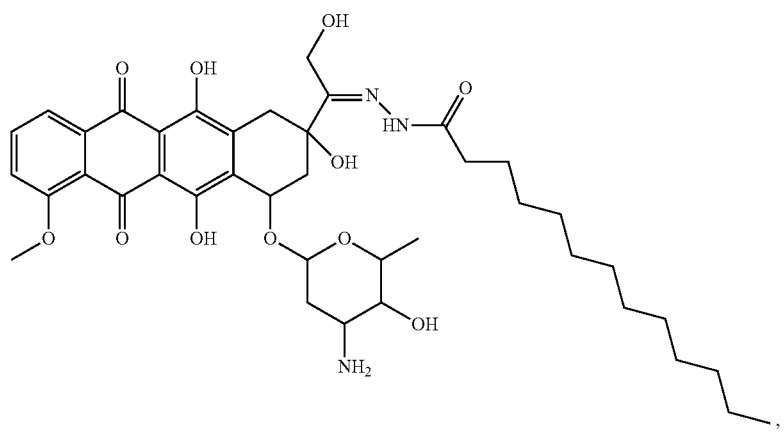

-continued
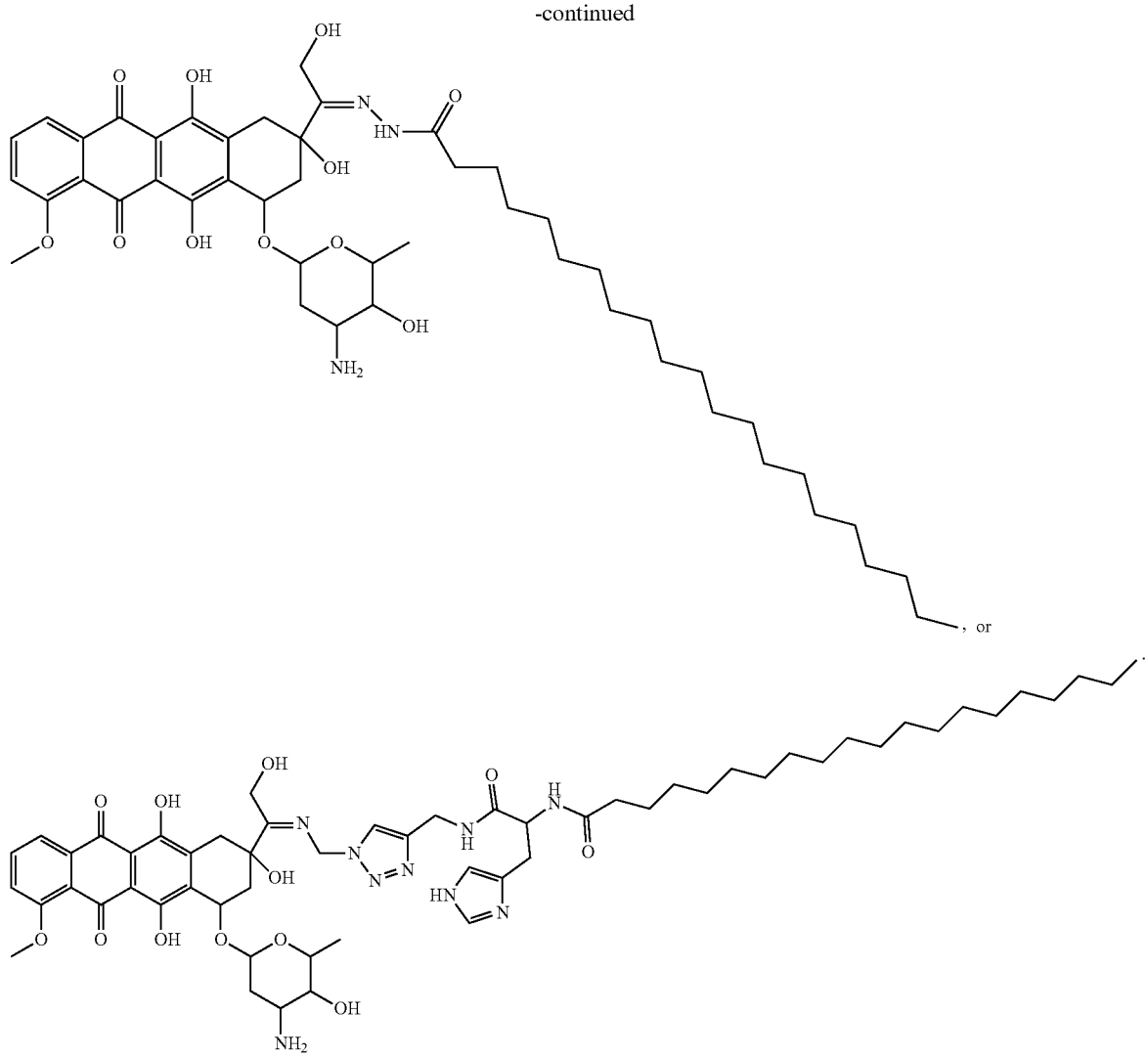
* * * * *